(12) United States Patent
Courtney et al.

(10) Patent No.: US 10,390,791 B2
(45) Date of Patent: Aug. 27, 2019

(54) ULTRASONIC PROBE WITH ULTRASONIC TRANSDUCERS ADDRESSABLE ON COMMON ELECTRICAL CHANNEL

(71) Applicant: Sunnybrook Health Sciences Centre, Toronto (CA)

(72) Inventors: Brian Courtney, Toronto (CA); Amandeep Thind, Toronto (CA)

(73) Assignee: SUNNYBROOK HEALTH SCIENCES CENTRE, Toronto, ON (CA)

(*) Notice: Subject to any disclaimer, the term of this patent is extended or adjusted under 35 U.S.C. 154(b) by 226 days.

(21) Appl. No.: 15/632,721

(22) Filed: Jun. 26, 2017

(65) Prior Publication Data

US 2018/0008230 A1    Jan. 11, 2018

Related U.S. Application Data

(63) Continuation of application No. 13/363,229, filed on Jan. 31, 2012, now Pat. No. 9,700,280.

(60) Provisional application No. 61/437,758, filed on Jan. 31, 2011.

(51) Int. Cl.
| | |
|---|---|
| *A61B 8/00* | (2006.01) |
| *A61B 8/12* | (2006.01) |
| *A61B 8/14* | (2006.01) |
| *B06B 1/06* | (2006.01) |
| *G10K 11/35* | (2006.01) |

(52) U.S. Cl.
CPC .............. *A61B 8/12* (2013.01); *A61B 8/14* (2013.01); *A61B 8/445* (2013.01); *A61B 8/4466* (2013.01); *B06B 1/06* (2013.01); *G10K 11/352* (2013.01)

(58) Field of Classification Search
CPC .. A61B 8/12; A61B 8/445; A61B 8/14; A61B 8/4466; G10K 11/352; B06B 1/06
See application file for complete search history.

(56) References Cited

U.S. PATENT DOCUMENTS

| | | | | |
|---|---|---|---|---|
| 4,841,979 | A * | 6/1989 | Dow | A61B 8/12 600/446 |
| 2008/0177139 | A1* | 7/2008 | Courtney | A61B 5/0062 600/109 |

FOREIGN PATENT DOCUMENTS

JP    H08-275946    10/1996

* cited by examiner

*Primary Examiner* — Peter Luong
(74) *Attorney, Agent, or Firm* — Hill & Schumacher

(57) ABSTRACT

Methods and apparatus are provided for electrically addressing multiple ultrasonic transducers that are connected to a common electrical channel and housed within an imaging probe. An imaging probe may comprise an imaging ultrasonic transducer and a moveable element for controlling the direction of an emitted imaging beam, and an angle sensing ultrasonic transducer, where the angle sensing ultrasonic transducer is configured for determining the direction of an ultrasonic imaging beam. The angle-sensing transducer may be configured to direct an angle sensing ultrasonic beam towards an acoustically reflective substrate and provide a signal by detecting a reflected ultrasonic beam reflected from the acoustically reflective substrate, where the acoustically reflective substrate is positioned relative to the movable element such that motion of the movable element produces a change in the signal.

24 Claims, 34 Drawing Sheets

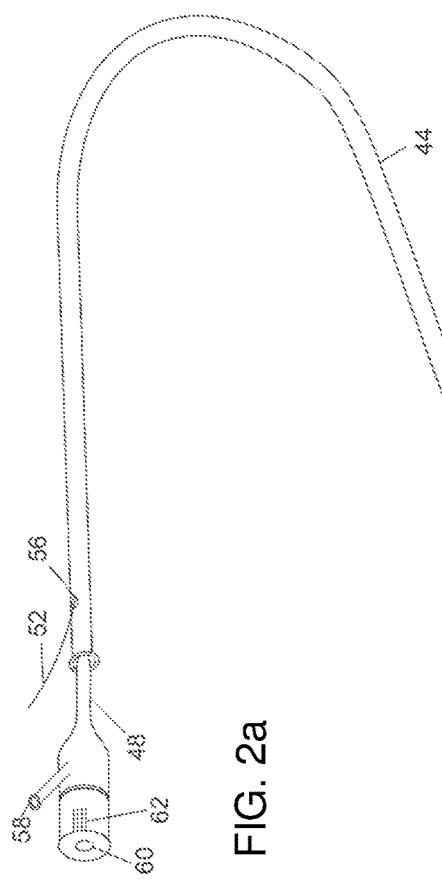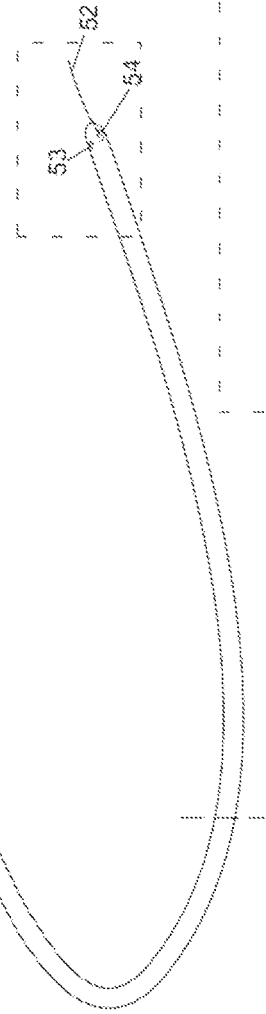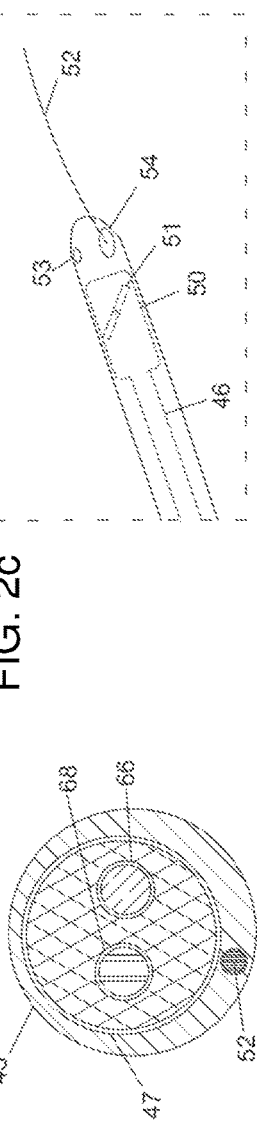
FIG. 2a
FIG. 2b
FIG. 2c

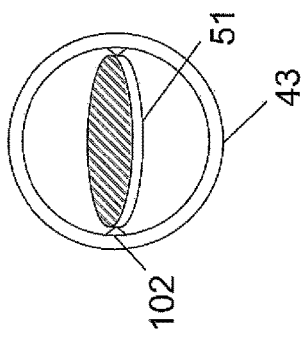
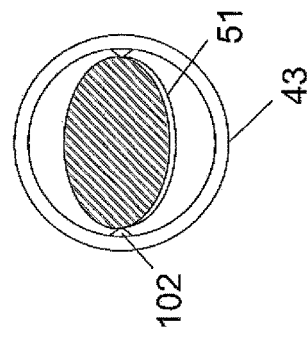
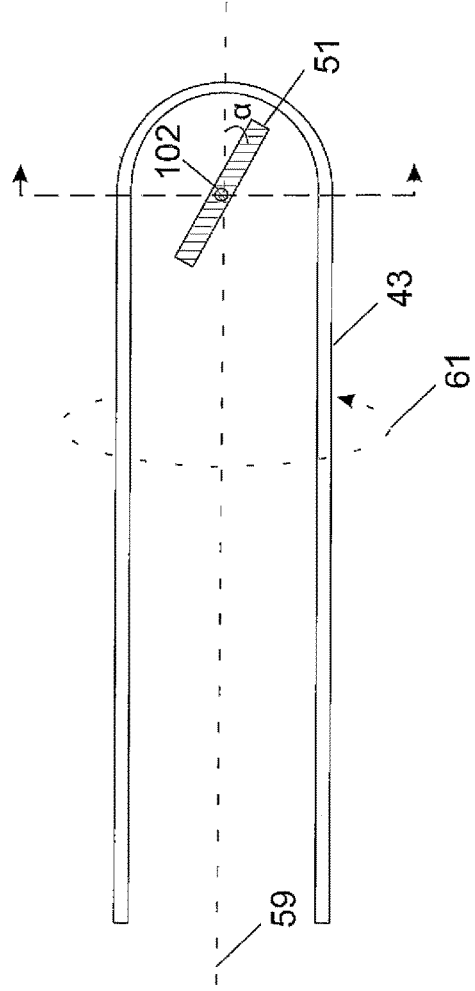
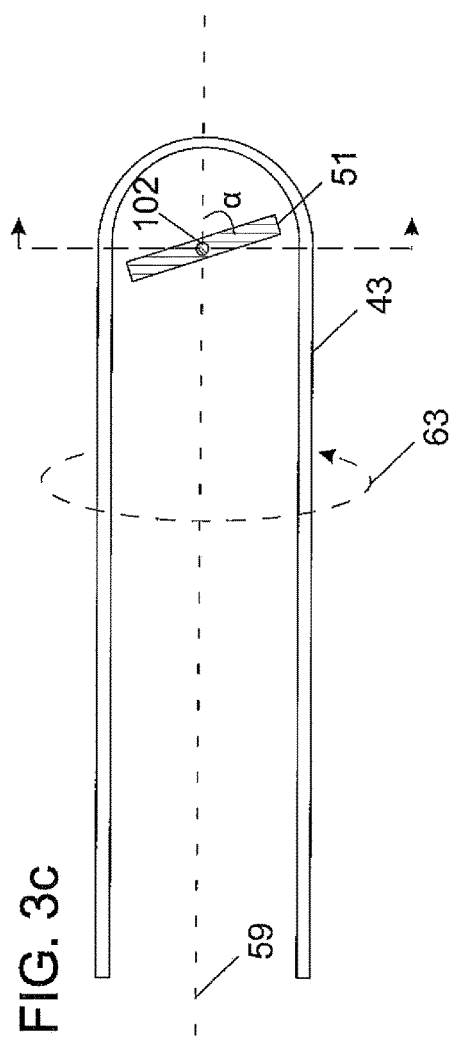
FIG. 3b
FIG. 3d
FIG. 3a
FIG. 3c

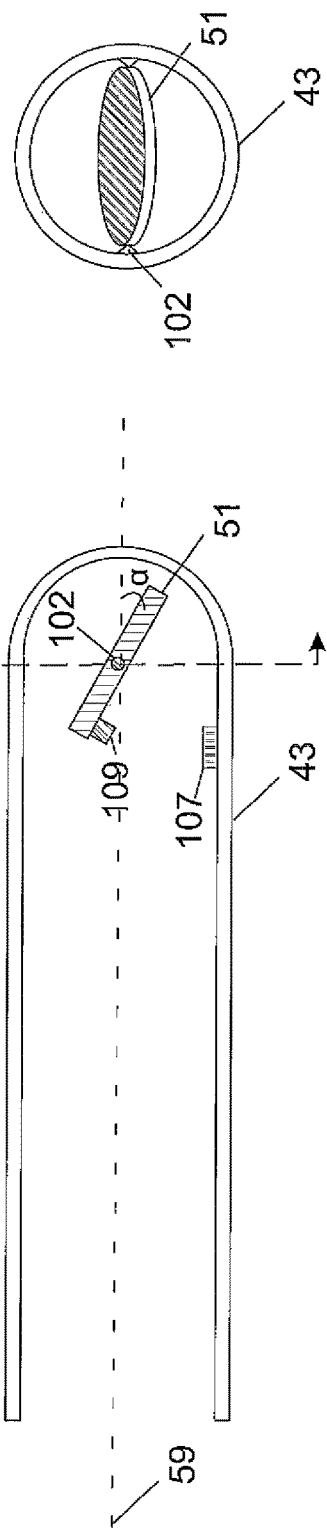
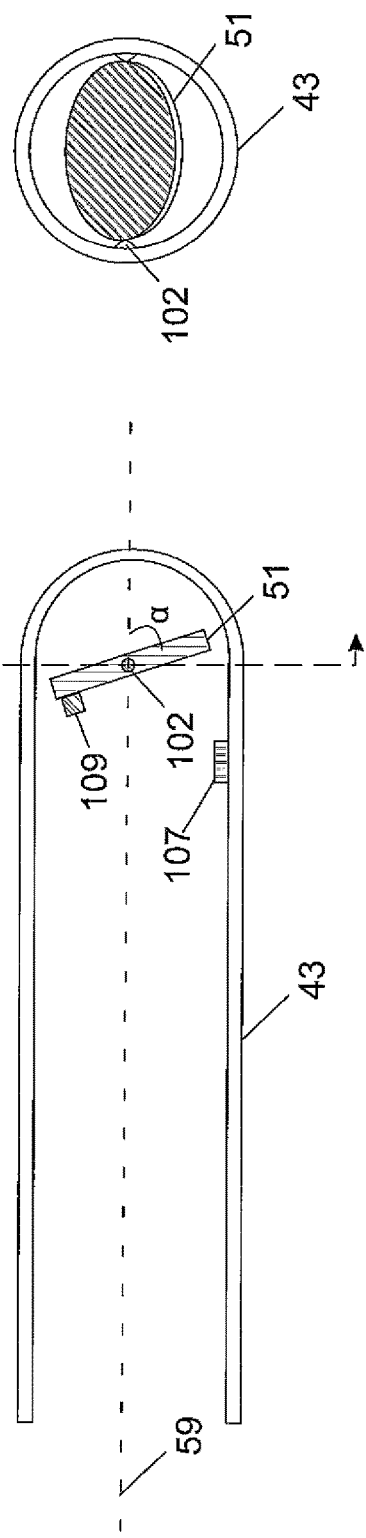

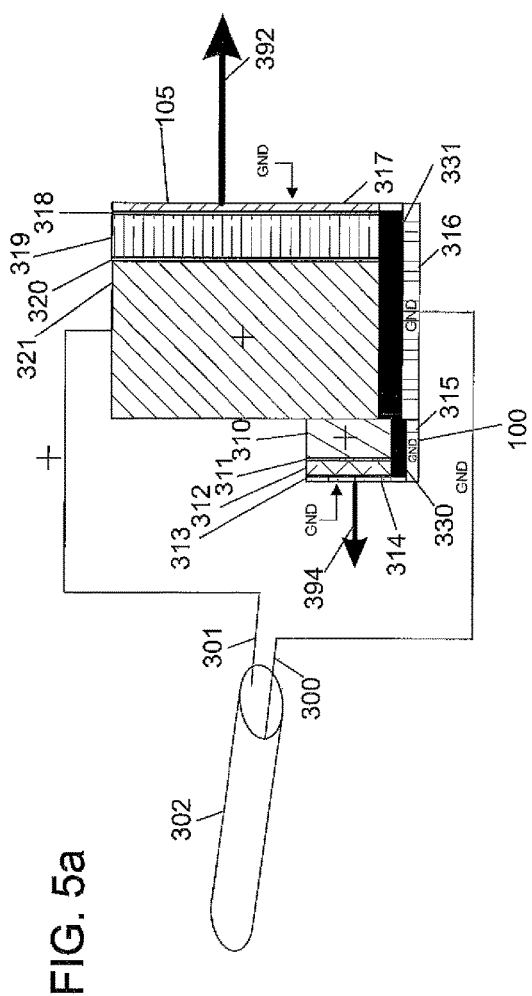
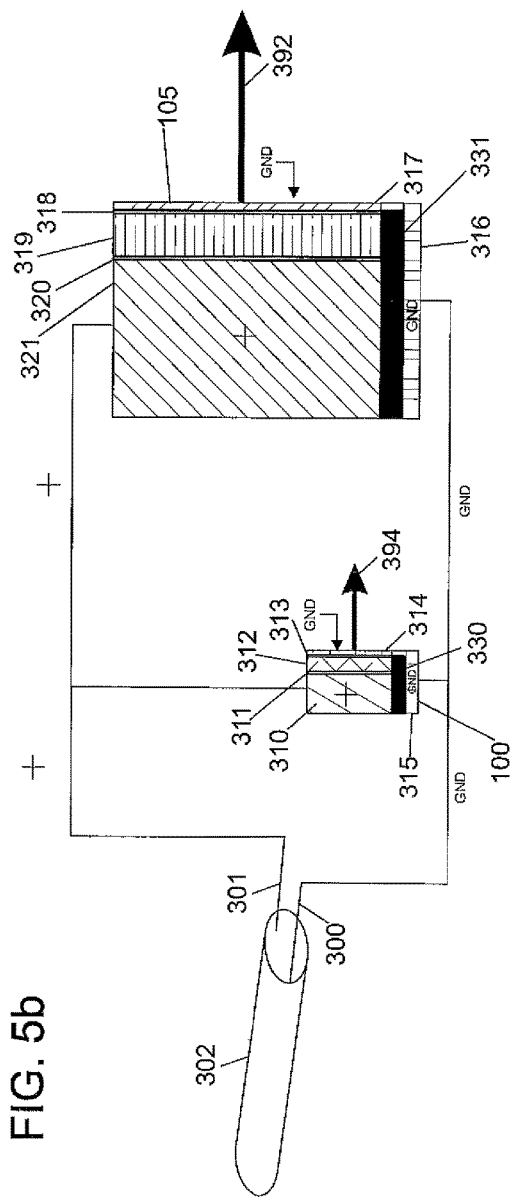

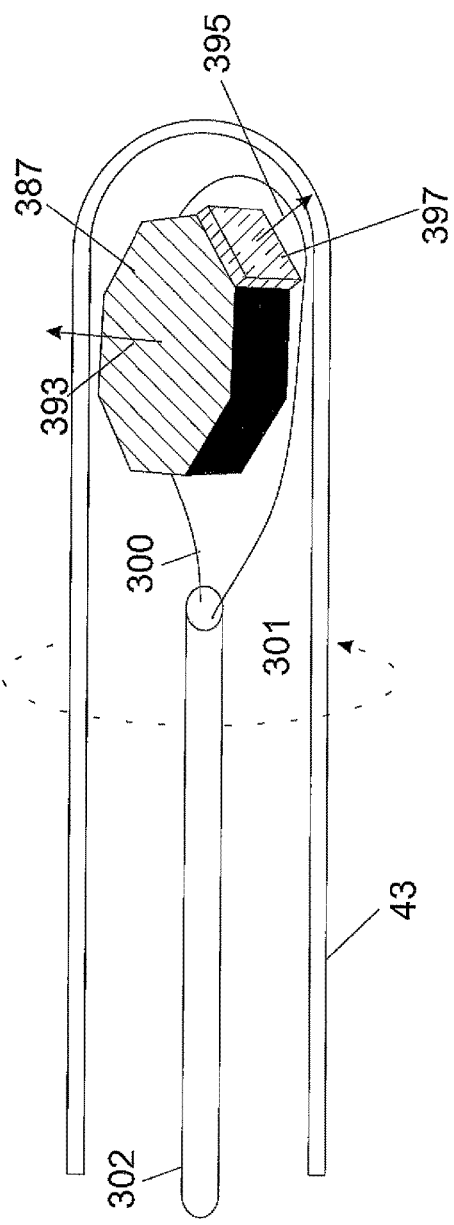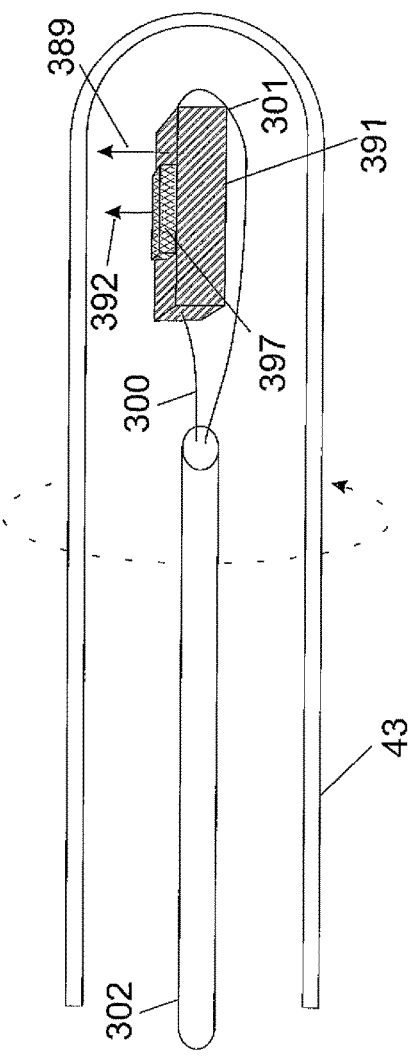

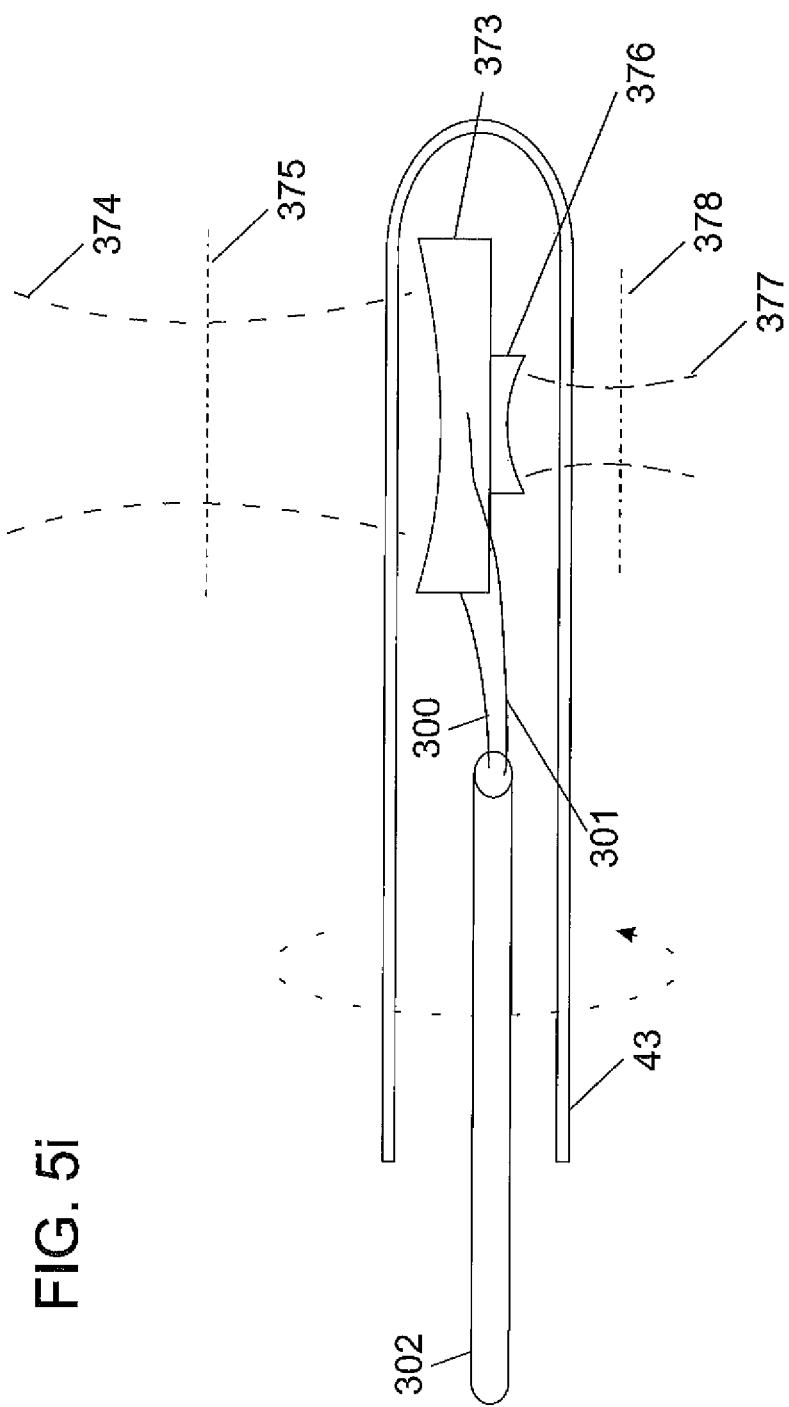

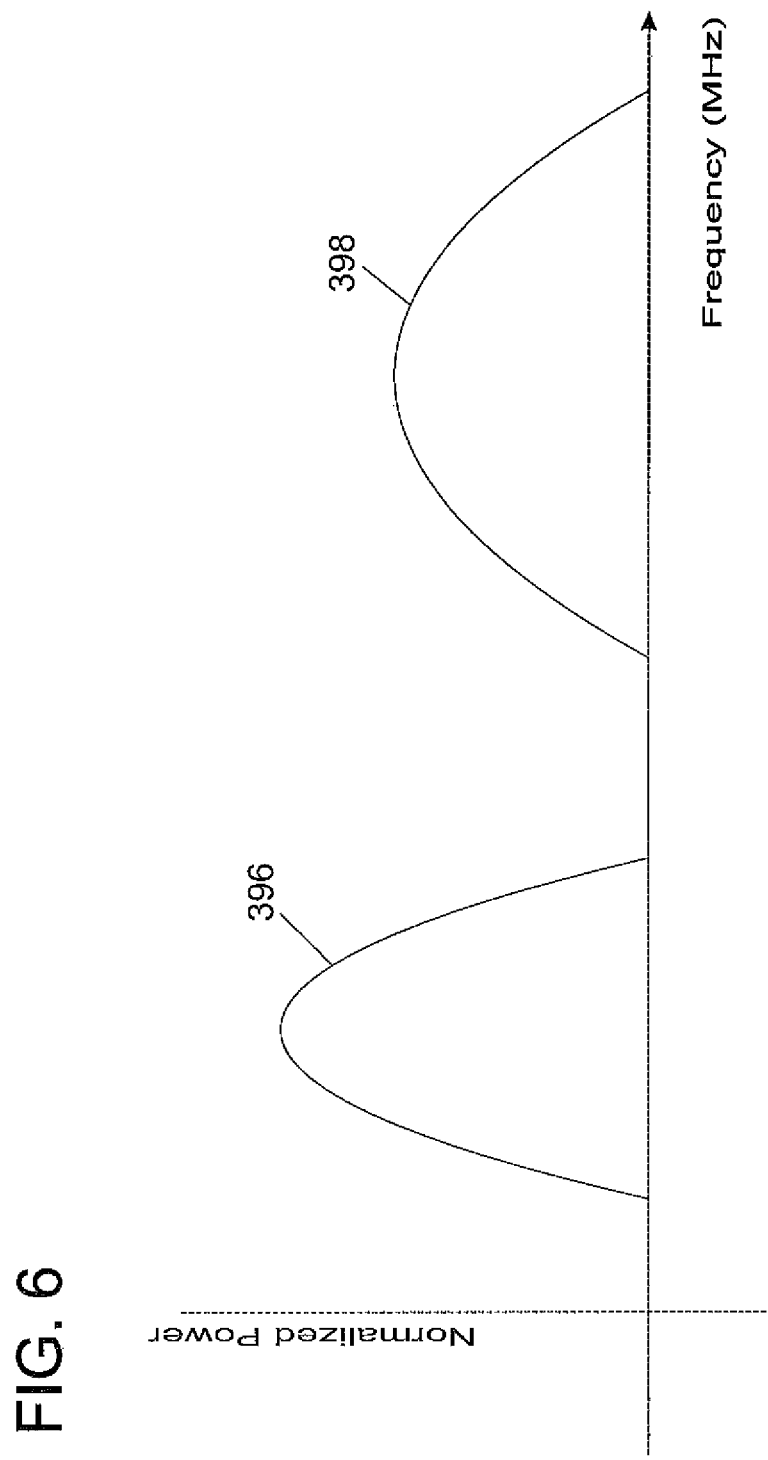

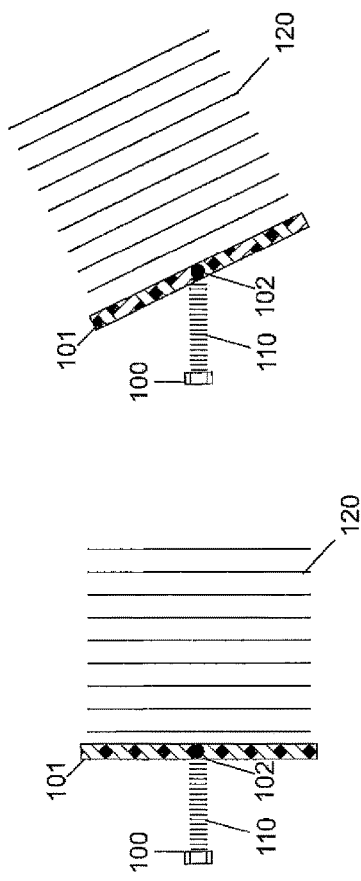
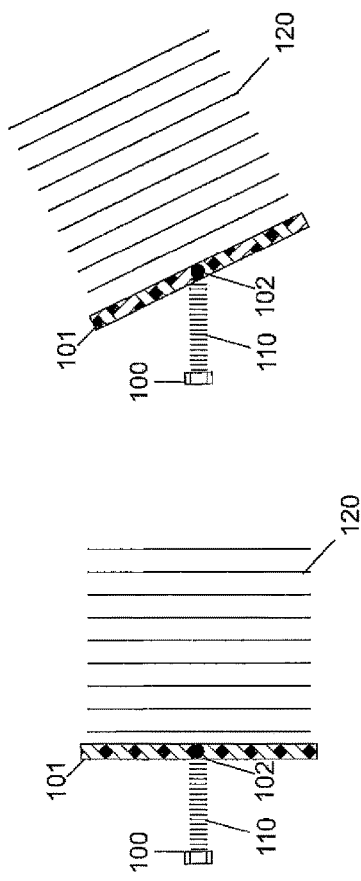
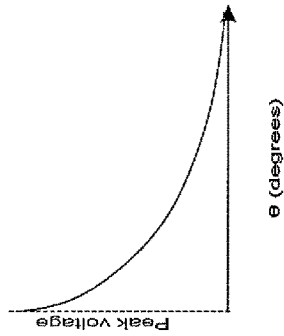
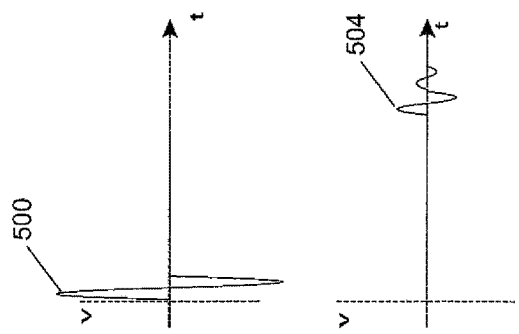
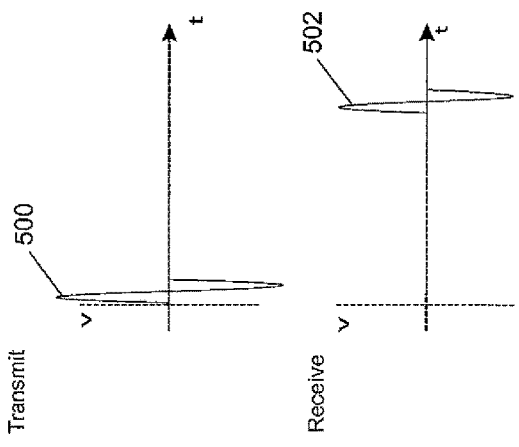

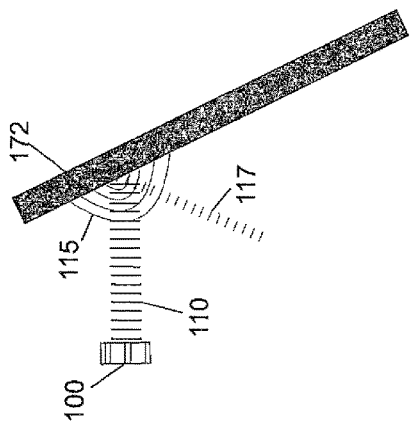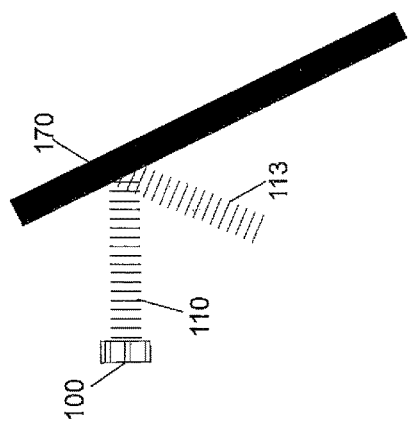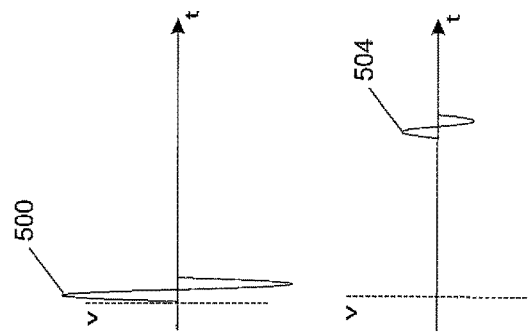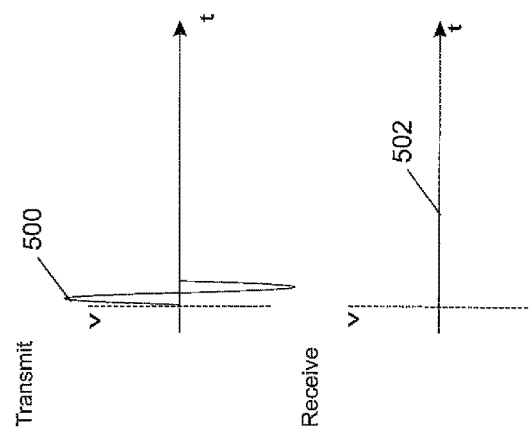

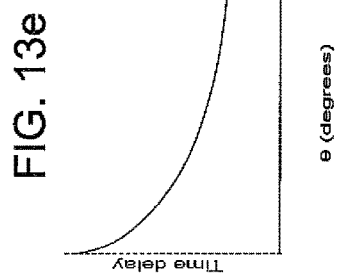
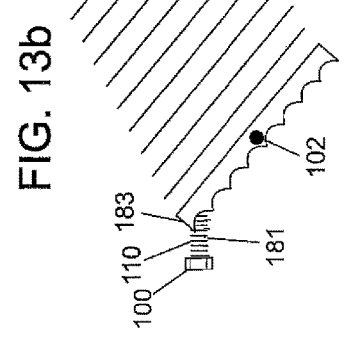
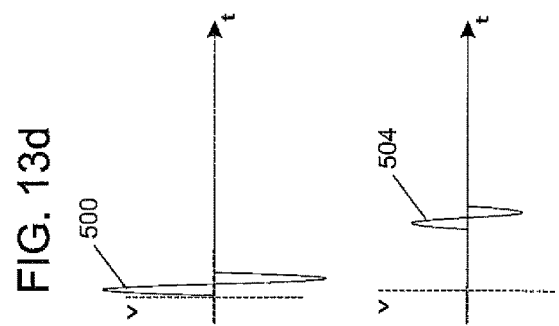
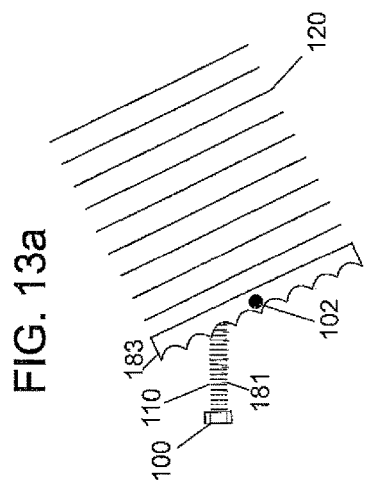
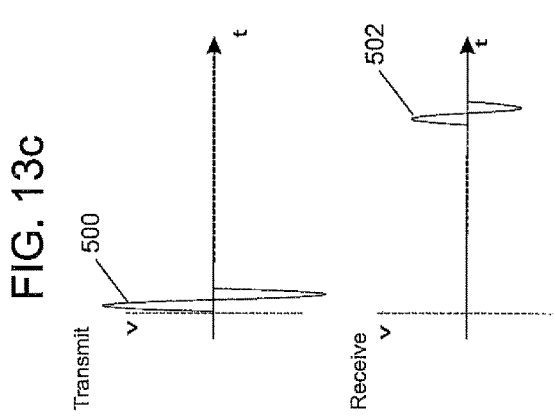

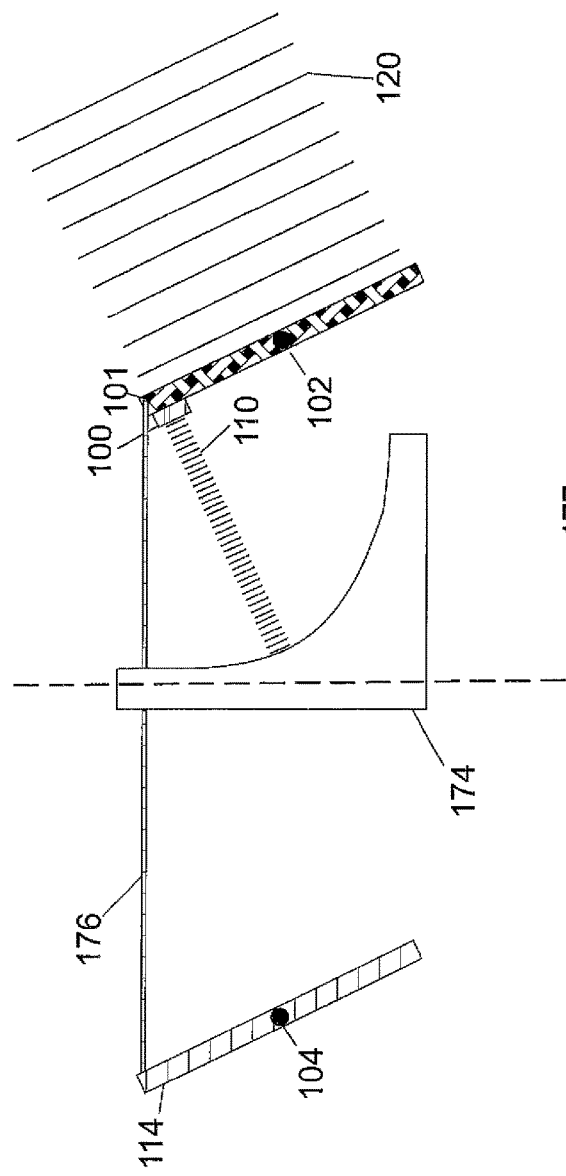
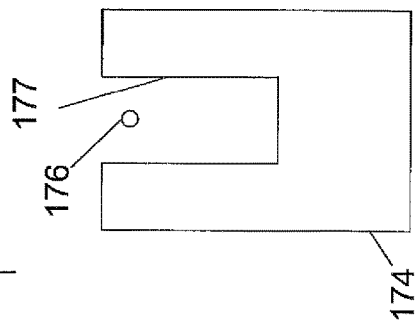
FIG. 18a
FIG. 18b

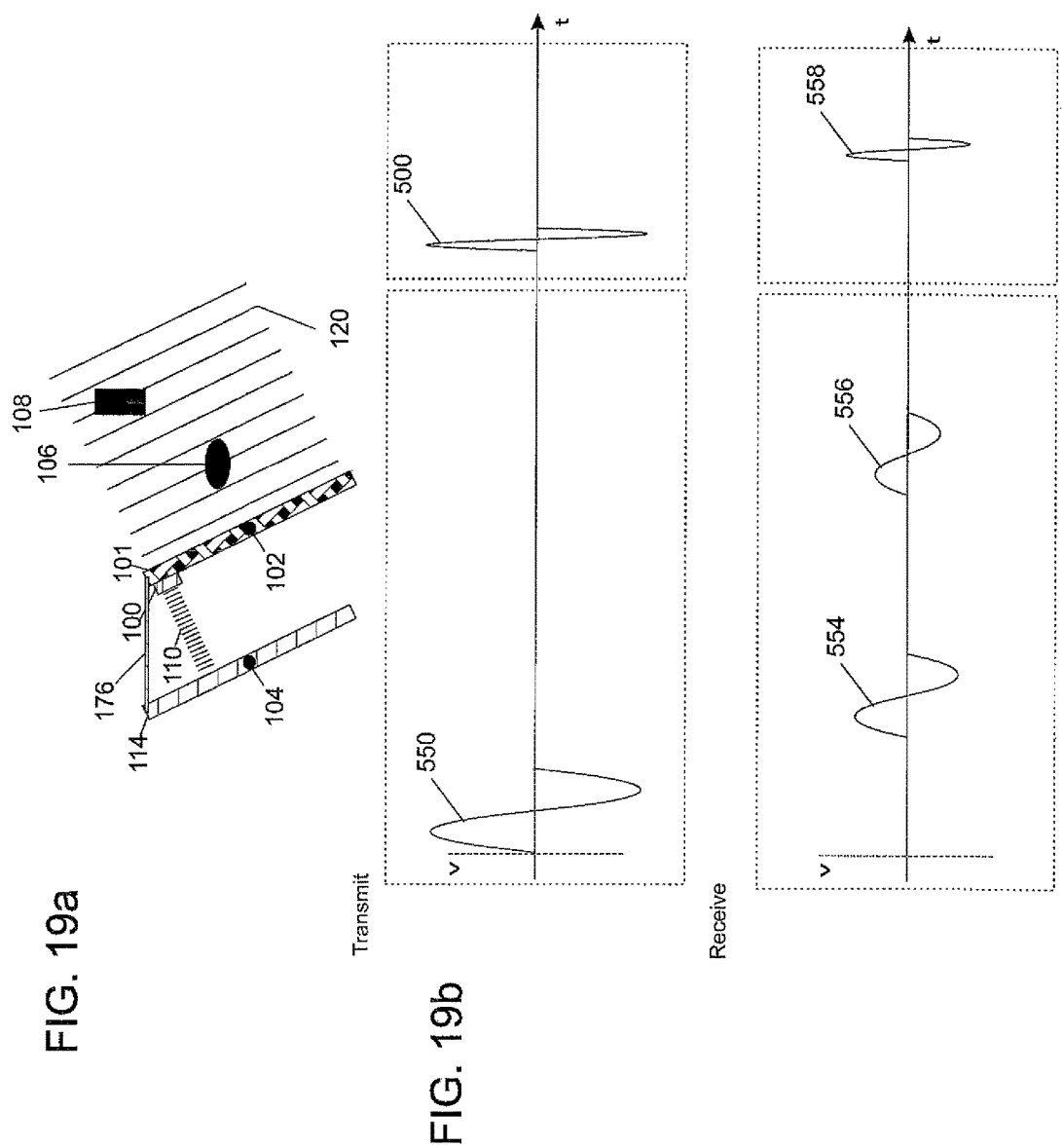

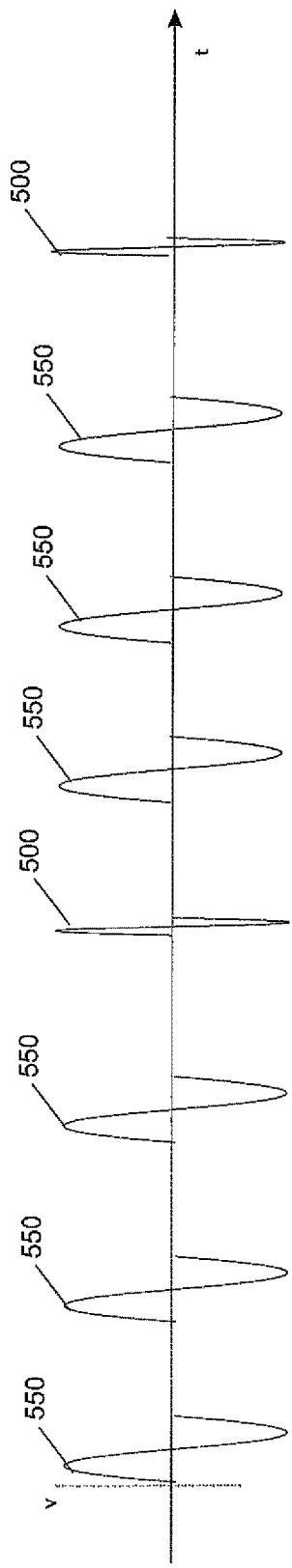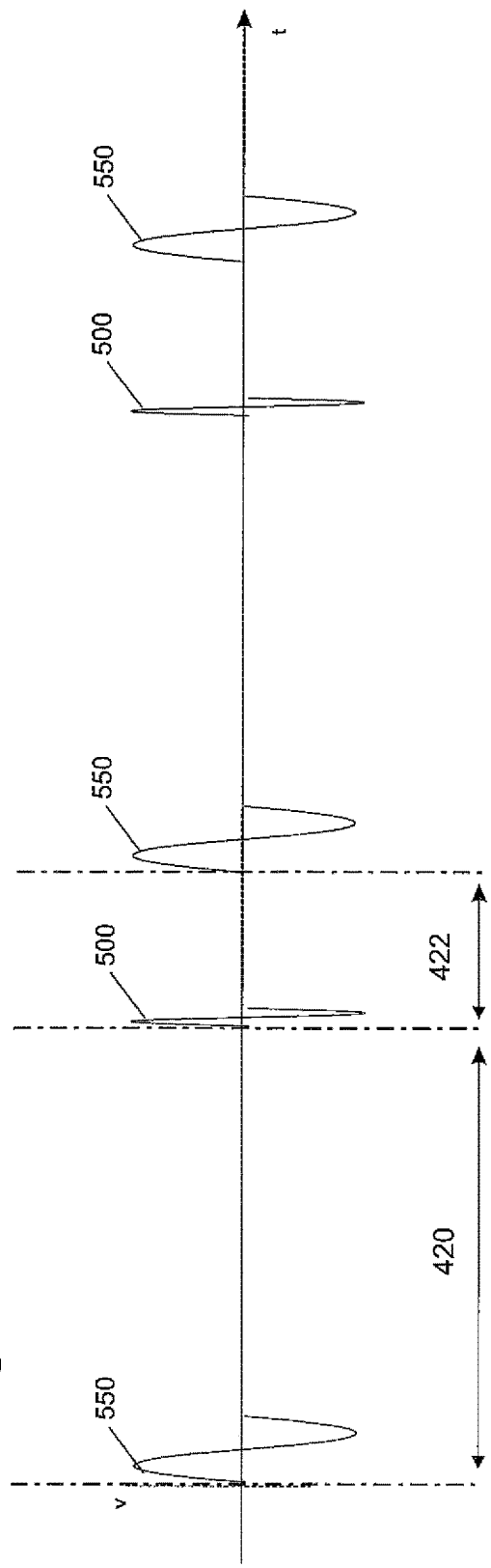

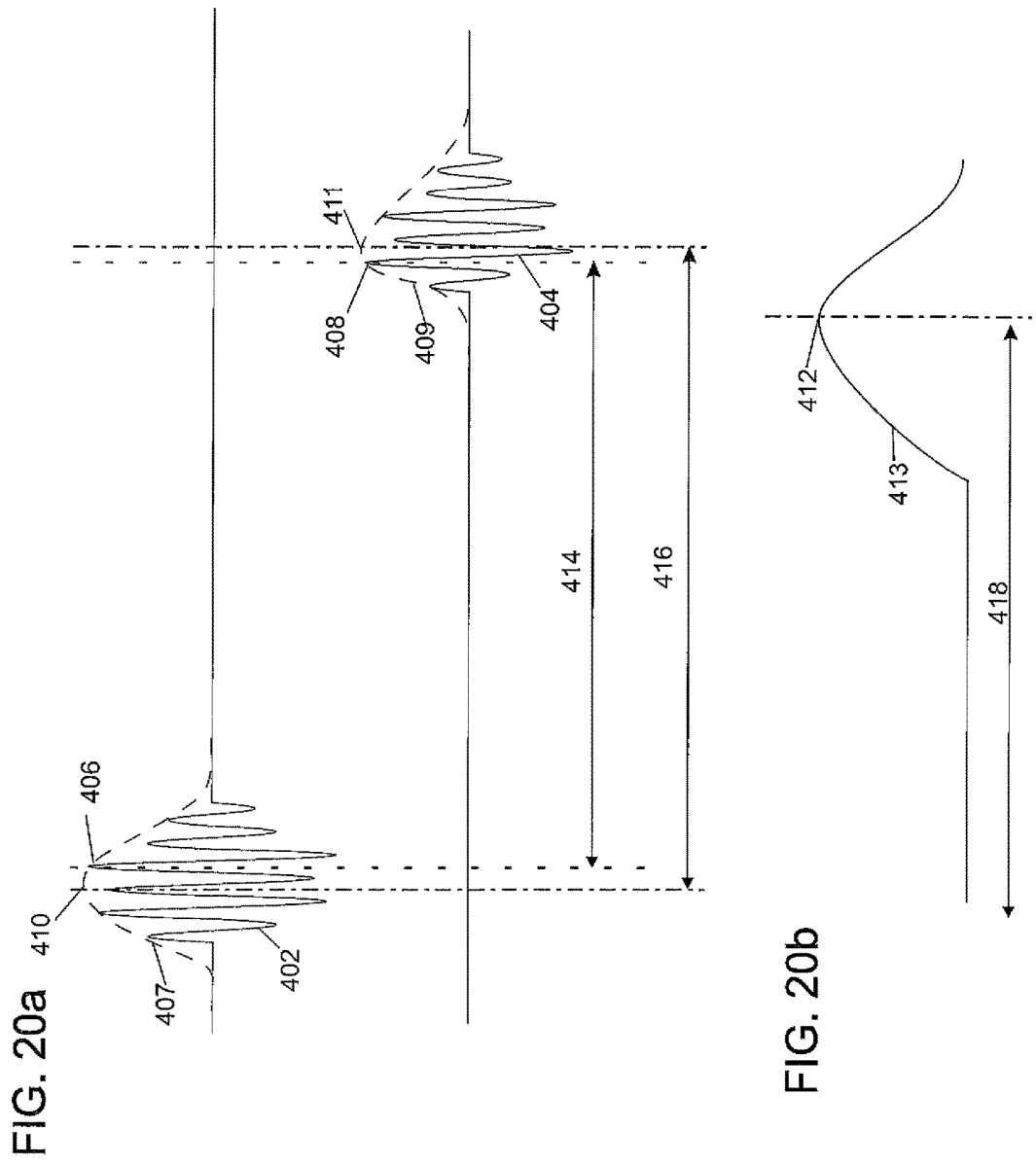

ULTRASONIC PROBE WITH ULTRASONIC TRANSDUCERS ADDRESSABLE ON COMMON ELECTRICAL CHANNEL

CROSS-REFERENCE TO RELATED APPLICATION

This application claims priority to U.S. Utility patent application Ser. No. 13/363,229, filed Jan. 31, 2012, titled "ULTRASONIC PROBE WITH ULTRASONIC TRANSDUCERS ADDRESSABLE ON COMMON ELECTRICAL CHANNEL", which claims the benefit of U.S. Provisional Application No. 61/437,758, titled "IMAGING PROBE WITH ULTRASONIC TRANSDUCERS ADDRESSABLE ON COMMON ELECTRICAL CHANNEL", and filed on Jan. 31, 2011, the entire contents of which are incorporated herein by reference.

BACKGROUND

The present disclosure relates to imaging systems and probes employing ultrasonic imaging transducers. The present disclosure also relates to methods of detecting changes in the angular orientation of movable elements employed for directing radiation from imaging transducers during minimally invasive imaging procedures. High resolution biomedical imaging serves numerous purposes, including assessing tissue structures and anatomy, planning and/or guiding interventions on localized regions of the body, and assessing the result of interventions that alter the structure, composition or other properties of a region.

High frequency ultrasound, in particular, has found significant use in intracardiac and intravascular applications. For these applications, ultrasound transducers are incorporated into a catheter or other device that can be inserted into a lumen or cavity within the body. Two important implementations of high frequency ultrasound are intravascular ultrasound (IVUS) for imaging blood vessels, and intracardiac echocardiography (ICE) for imaging cardiac chambers. Both ICE and IVUS are minimally invasive, and involve placing one or more ultrasound transducers inside a blood vessel or cardiac chamber to take high quality images of these structures.

Courtney et al. (US Patent Application Publication No. US20090264768) describe an intravascular/intracardiac echocardiography catheter capable of forward viewing via 3D ultrasound and/or optical imaging. This is achieved using a movable member to image at various angles. This device benefits from knowledge of the position and/or orientation of either the imaging mechanism itself or of a deflecting element, such as a mirror.

In order to correlate the images obtained using an imaging transducer with the orientation of the imaging probe, it is important to provide a mechanism for determining the relative angular orientation of the movable portion of an imaging system. This angular orientation determines an angle at which imaging energy is transmitted and/or received from the imaging probe. Courtney et al. disclose a number of angle detection mechanisms and methods. One method involves relating the rotational speed to the imaging angle, for example, using a look-up table. A series of electronic and electromechanical techniques are also described, including capacitive, resistive, electromagnetic, inductive, and strain gauge based techniques. Also described are techniques that employ diffuse scattering from a reflector using the primary imaging source. Also disclosed are optical and acoustic methods and mechanism that utilize a detection sensor that is separate from the primary imaging source to determine the imaging angle.

There are a number of limitations related to the techniques described above. For example, the use of a lookup table relating rotational speed to imaging angle may be prone to significant inaccuracy. Different orientations or situations may influence the relationship between imaging angle and rotational speeds. This may occur as a result of gravitational forces in different orientations, different temperature conditions, or stress on the catheter among others. Also, many techniques—predominantly those using modalities other than the imaging modality—may require the addition of significant complex components and energy sources.

SUMMARY

Methods and apparatus are provided for electrically addressing multiple ultrasonic transducers that are connected to a common electrical channel and housed within an imaging probe. An imaging probe may comprise an imaging ultrasonic transducer and a moveable element for controlling the direction of an emitted imaging beam, and an angle sensing ultrasonic transducer, where the angle sensing ultrasonic transducer is configured for determining the direction of an ultrasonic imaging beam. The angle-sensing transducer may be configured to direct an angle sensing ultrasonic beam towards an acoustically reflective substrate and provide a signal by detecting a reflected ultrasonic beam reflected from the acoustically reflective substrate, where the acoustically reflective substrate is positioned relative to the movable element such that motion of the movable element produces a change in the signal.

Accordingly, in a first aspect, there is provided an imaging probe comprising: a longitudinal body; a first ultrasonic transducer provided within the longitudinal body, wherein the first ultrasonic transducer is located remote from a proximal end of the longitudinal body, and wherein the first ultrasonic transducer is configured to deliver an ultrasonic imaging beam to a region outside of the longitudinal body and to receive reflected ultrasonic imaging energy from the region; a second ultrasonic transducer housed within the longitudinal body; and electrically conductive paths extending through the longitudinal body and defining a common electrical channel; wherein the first ultrasonic transducer and the second ultrasonic transducer are connected to the common electrical channel, and wherein the common electrical channel is electrically connectable to an image processing system.

In another aspect, there is provided an ultrasonic probe comprising: a longitudinal body; a first ultrasonic transducer provided within the longitudinal body, wherein the first ultrasonic transducer is located remote from a proximal end of the longitudinal body, and wherein the first ultrasonic transducer is configured to deliver an ultrasonic beam to a region outside of the longitudinal body; an additional ultrasonic transducer provided within the longitudinal body; an electrically conductive paths extending through the longitudinal body and defining a common electrical channel; wherein the first ultrasonic transducer and the additional ultrasonic transducer are connected to the common electrical channel, and wherein the common electrical channel is electrically connectable to an external processing system.

In another aspect, there is provided an ultrasonic angle detection device for determining an angle of a pivotable member, wherein the pivotable member is pivotally coupled to a solid support, the device comprising: an electrically addressable ultrasonic transducer attached to the pivotable member, wherein the ultrasonic transducer is configured to emit ultrasonic pulses in a direction that is dependent on an orientation of the pivotable member; and an acoustically reflective substrate fixed relative to the solid support and having a surface curvature selected to substantially retroreflect the ultrasonic pulses back to the ultrasonic transducer over a defined angular range of the pivotable member, such that a distance between the ultrasonic transducer and the acoustically reflective substrate, as determined along a beam path of the ultrasonic pulses, varies over the angular range.

A further understanding of the functional and advantageous aspects of the disclosure can be realized by reference to the following detailed description and drawings.

BRIEF DESCRIPTION OF THE DRAWINGS

Embodiments of the disclosure will now be described, by way of example only, with reference to the drawings, in which:

FIG. 2a is a perspective drawing of a flexible imaging probe with an adapter, conduit, and imaging assembly.

FIG. 2b is a cross sectional view of the mid-section of the imaging probe of FIG. 2a taken along the dotted line.

FIG. 2c is a magnified and expanded drawing of the distal region of the imaging probe of FIG. 2a.

FIGS. 3a-3g describe embodiments of techniques for causing tilting of a tiltable member.

FIG. 3a shows a longitudinal cutaway of a catheter in which the tilting is caused by centripetal motion.

FIG. 3b shows a cross-sectional cutaway of the catheter shown in FIG. 3a.

FIG. 3c shows the catheter of FIG. 3a and the resulting tilting caused by rotating the scanning assembly at a faster rate than that of FIG. 3a.

FIG. 3d shows a cross-sectional cutaway of the catheter shown in FIG. 3c.

FIG. 3e shows a longitudinal cutaway of a catheter in which the tilting is controlled using one or more magnets.

FIG. 3f shows a cross-sectional cutaway of the catheter in FIG. 3e.

FIG. 3g shows the catheter of FIG. 3e and the resulting deflection caused by magnetism.

FIG. 3h shows a cross-sectional cutaway of the catheter in FIG. 3g.

FIGS. 4a and 4b show the measurement of the tilt of the tiltable component at two different angular orientations. FIGS. 4c and 4d plot the time dependence of the transmitted and received ultrasonic pulses for the angular orientations shown in FIGS. 4a and 4b, respectively. FIG. 4e plots the dependence of the time delay of the ultrasonic beam on the tilt angle.

FIG. 4f shows a body that has a similar dimension in the range direction relative to the elevation direction, while

FIGS. 5a and 5b show connection schemes of ultrasound transducers to produce acoustic energy through multiple ultrasound transducers via a single electrical connection. FIG. 5a shows a case where an imaging transducer and an angle detection transducer are directly bonded together. FIG. 5b shows a case where an imaging transducer and an angle detection transducer are physically separated, but connected electrically. FIGS. 5c-5e illustrate embodiments in which two imaging ultrasonic transducers are housed within a sheath and connected to a common electrical channel for simultaneous imaging in antiparallel (FIG. 5c) and orthogonal (FIGS. 5d-5e), and parallel (FIG. 5f). FIG. 5i shows an arrangement with focused ultrasound transducers.

FIG. 6 shows a separation between the active bandwidths of two ultrasound transducers connected to a common channel.

FIGS. 8a and 8b show the measurement of the tilt angle of the tiltable mirror at two different angular orientations. FIGS. 8c and 8d plot the time dependence of the transmitted and received ultrasonic pulses for the angular orientations shown in FIGS. 8a and 8b, respectively. FIG. 8e plots the dependence of the time delay of the ultrasonic beam on the deflection angle.

FIGS. 9a and 9b show the measurement of tilt of the mirror at two different angular orientations. FIGS. 9c and 9d plot the time dependence of the transmitted and received ultrasonic pulses for the angular orientations shown in FIGS. 9a and 9b, respectively. FIG. 9e plots the dependence of the time delay of the angle detecting ultrasonic beam on the tilt angle.

FIGS. 10a-10e demonstrate the use of a high frequency ultrasound transducer to estimate the deflection angle of a tiltable component using a method that assesses the intensity of the received signal. FIGS. 10a and 10b show the measurement of the tilt of a tiltable component at two different angular orientations. FIGS. 10c and 10d plot the time dependence of the transmitted and received ultrasonic pulses for the angular orientations shown in FIGS. 10a and 10b, respectively. FIG. 10e plots the dependence of the peak voltage relating to the received ultrasonic beam on the deflection angle.

FIGS. 11a and 11b show (a) the use of a surface comprising a specular reflector in comparison with (b) a diffuse reflector. FIGS. 11c and 11d plot the time dependence of the transmitted and received ultrasonic pulses for the angular orientations shown in FIGS. 11a and 11b, respectively.

FIGS. 12c and 12d plot the time dependence of the transmitted and received ultrasonic pulses for the angular orientations shown in FIGS. 12a and 12b, respectively.

FIGS. 13a-e show a disc with curved features to increase the range of angles that can be detected using a time of flight method, shown in (a) and (b) at two different angular orientations. FIGS. 13c and 13d plot the time dependence of the transmitted and received ultrasonic pulses for the angular orientations shown in FIGS. 13a and 13b, respectively. FIG. 13e plots the dependence of the time delay of the ultrasonic beam on the deflection angle.

FIGS. 14c and 14d plot the time dependence of the transmitted and received ultrasonic pulses for the angular orientations shown in FIGS. 14a and 14b, respectively.

FIGS. 15c and 15d plot the time dependence of the transmitted and received ultrasonic pulses for the angular orientations shown in FIGS. 15a and 15b, respectively.

FIGS. 16c and 16d plot the time dependence of the transmitted and received ultrasonic pulses for the angular orientations shown in FIGS. 16a and 16b, respectively.

FIGS. 17c and 17d plot the time dependence of the transmitted and received ultrasonic pulses for the angular orientations shown in FIGS. 17a and 17b, respectively.

FIGS. 18a-b show the use of the curved surface shown in FIGS. 15a-e with a mechanically coupled acoustically passive component similar to that shown in FIGS. 16 and 17. FIG. 18a shows a view with the same perspective shown in FIGS. 17a-d. FIG. 18b shows a view cut through the hatched line from FIG. 18a.

FIGS. 18c and 18e show the tiltable member at two different positions. FIGS. 18d and 18f show views cut through the hatched line from FIGS. 18c and 18e respectively. FIGS. 18g and 18h show timing diagrams from the scenarios described in FIGS. 18d and 18f respectively. FIG. 18i shows a relationship between the received time delay and the tilt angle.

FIGS. 19a-g show a sample pulse sequence and corresponding received signal from both the imaging transducer and the deflection angle transducer on a single channel using multiple methods. FIG. 19a shows the measurement of two features, and FIG. 19b shows how the signals from the two features and the signal from the angle detection transducer can be extracted based on an interleaved pulsing scheme.

FIG. 19c shows an example using either or both of: prior knowledge of distance ranges and using spectral methods. FIG. 19d shows how the signals from the two features and the signal from the angle detection transducer can be extracted based on whether or not they are beyond the maximum distance range used in the angle detection scheme. FIGS. 19e shows an example of the use of spectral methods to separate angle detection information from imaging information.

FIG. 19f shows a transmit pulse sequence where multiple imaging pulses are transmitted between single angle detection pulses. FIG. 19g shows a transmit pulse sequence where there is a long time delay between the imaging pulse and the subsequent angle detection pulse, and a short time delay between the angle detection pulse and the subsequent imaging pulse.

FIGS. 20a-b show different estimation methods for determining a distance as detected by an angle detection transducer. FIG. 20a shows an example of the detection of the distance based on the use of radio-frequency (RF) peak detection methods and envelope detection methods, while FIG. 20b example illustrates the detection of the distance based on the use of cross correlation methods. p

DETAILED DESCRIPTION

Figure 1:
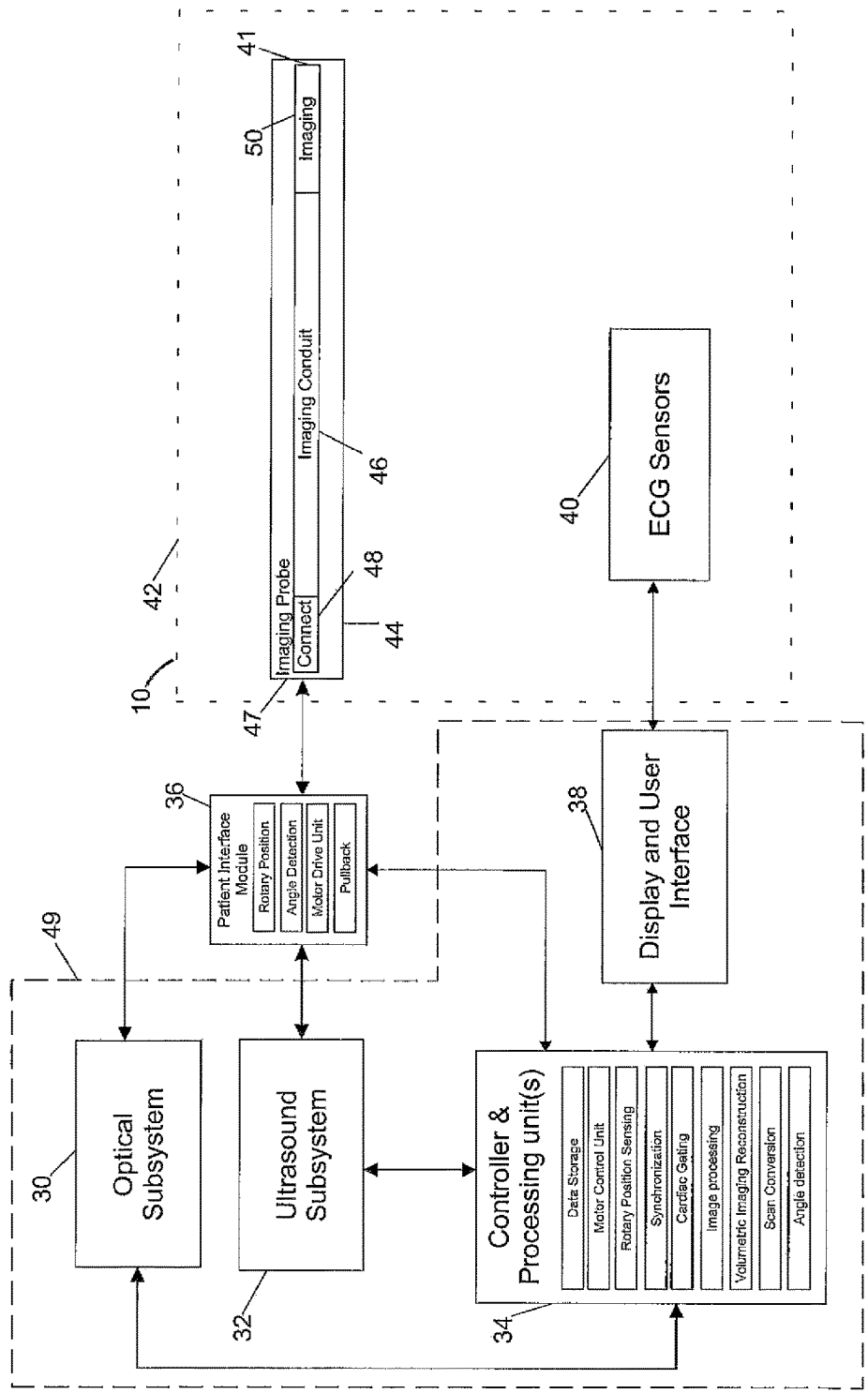
FIG. 1 is a schematic of an imaging system including ultrasound and optical components.

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure. It should be understood that the order of the steps of the methods disclosed herein is immaterial so long as the methods remain operable. Moreover, two or more steps may be conducted simultaneously or in a different order than recited herein unless otherwise specified.

As used herein, the terms, "comprises" and "comprising" are to be construed as being inclusive and open ended, and not exclusive. Specifically, when used in the specification and claims, the terms, "comprises" and "comprising" and variations thereof mean the specified features, steps or components are included. These terms are not to be interpreted to exclude the presence of other features, steps or components.

As used herein, the term "example" means "serving as an example, instance, or illustration," and should not be construed as preferred or advantageous over other configurations disclosed herein.

As used herein, the terms "about" and "approximately", when used in conjunction with ranges of dimensions of particles, compositions of mixtures or other physical properties or characteristics, are meant to cover slight variations that may exist in the upper and lower limits of the ranges of dimensions so as to not exclude embodiments where on average most of the dimensions are satisfied but where statistically dimensions may exist outside this region. It is not the intention to exclude embodiments such as these from the present disclosure. For example, in embodiments of the present disclosure, dimensions of components of the imaging probe are given but it will be understood that these are not meant to be limiting.

As used herein, the term "high resolution imaging" generally refers to optical imaging methods and high frequency ultrasound, the latter of which typically involving frequencies of greater than 3 MHz, and more typically involving frequencies in the range of 5 to 100 MHz.

As used herein, the terms "imaging radiation" and "imaging energy" refer to electromagnetic or acoustic radiation, or both. Specifically, electromagnetic radiation may span the ultraviolet, visible, and or infrared spectrum of wavelengths.

As used herein, the term "deflect" refers to a change in at least an angular orientation of an object relative to. In one example, a deflection may be a change in the tilt of a tiltable component or a change in an angular orientation of a movable member. As used herein, the term "tilt" refers to the angular orientation of an object. A change in angular orientation, as defined by a change in a tilt angle, may be relative to another portion of an object if the object is deformable, or relative to another object within an assembly of objects. For example, a component mounted on a pivot mechanism may tilt by pivoting around an axis of the pivot mechanism. Alternatively, a component mounted on a deformable component or integrated as part of a deformable component may experience a tilt as a result of deformation of the deformable component.

As used herein, the term "move" refers to a change in either an angular orientation of an object, a position of an object or both the angular orientation and position of an object. For example, the movement of an object may occur as a result of a tilting an object or pivoting of an object around an axis. Movement may also occur as a result of a deformation an object or a deformable portion of an object. Movement may also occur as a result of translation of an object. The movement of an object may be in absolute terms, relative to another portion of an object if the object is deformable, or relative to another object within an assembly of objects.

As used herein, the term "electrical channel" refers electrically conductive paths that are suitable for delivering electrical energy to, or detecting electrical signals from, an electrical element, such as an ultrasonic transducer. An example of an electrical channel includes two conductors, such as wires, that are contacted with an electrical element such that when a voltage difference is applied between the conductors, a corresponding voltage is applied across the electrical element.

Embodiments of the disclosure provide apparatus and methods for the non-contact detection of a change in orientation or position of a movable member. An ultrasonic transducer is employed to generate an incident ultrasonic beam and to detect a reflected ultrasonic beam, where the deflection of a deflectable member produces a change in one or more of: a) the intensity, b) the time delay, or c) the spectral content of the reflected beam. The proceeding disclosure describes and illustrates, through examples, the application of various embodiments to minimally invasive imaging systems and methods. However, it is to be understood that these applications are merely non-limiting examples, and the embodiments disclosed here are applicable and adaptable to a wide range of uses and applications.

Before describing example embodiments and their application to minimally invasive imaging systems, a brief review of minimally invasive imaging systems is provided with reference to FIGS. 1 to 3, by way of example. Referring first to FIG. 1, an imaging system is shown at 10 comprising imaging probe 44, which connects via patient interface module 36 to image processing and display system 49. Image processing and display system 49 includes hardware to support one or more imaging modalities, such as ultrasound, optical coherence tomography, angioscopy, infrared imaging, near infrared imaging, Raman spectroscopy-based imaging, or fluorescence imaging. Specific embodiments of ultrasonic imaging probes and combined ultrasonic and optical imaging probes are disclosed by Courtney et al. in US Patent Publication No. 20080177183, titled "Imaging Probe with Combined Ultrasounds and Optical Means of Imaging" and filed on Jan. 22, 2008, US Patent Publication No. 20080177138, titled "Scanning Mechanisms for Imaging Probe" and filed on Jan. 22, 2008 and US Patent Publication No. 20090264768, titled "Scanning Mechanisms for Imaging Probe" and filed on Mar. 27, 2009, each of which are incorporated herein by reference in their entirety.

Controller and processing unit 34 is employed to facilitate the coordinated activity of the many functional units of the system, and may contain some or all of the components shown in the Figure and listed herein. An operator interacts with system 50 via display and/or user interface 38. System 10 may further include electrode sensors 40 to acquire electrocardiogram signals from the body of the patient being imaged. The electrocardiogram signals may be used to time the acquisition of imaging data in situations where cardiac motion may have an impact on image quality. The electrocardiogram may also serve as a trigger for when to begin an acquisition sequence, such as when to begin changing the speed of rotation of a motor in order to cause a desired scan pattern to take effect. For example, electrocardiogram triggered initiation of an imaging sequence may enable images to be acquired during a particular phase of the cardiac cycle, such as systole or diastole.

Optical subsystem 30, if included in a particular implementation of an imaging system, may include any or all of the following components: interferometer components, one or more optical reference arms, optical multiplexors, optical demultiplexers, light sources, photodetectors, spectrometers, polarization filters, polarization controllers, timing circuitry, analog to digital converters, parallel processing arrays and other components known to facilitate any of the optical imaging techniques. Ultrasound subsystem 32 may include any or all of the following components: pulse generators, electronic filters, analog to digital converters, parallel processing arrays, envelope detectors, amplifiers including time gain compensation amplifiers and other components known to facilitate acoustic imaging techniques.

Controller and processing units 34, if included in a particular implementation of the imaging system, serve multiple purposes. Those skilled in the art will appreciate that specific components required depend on the needs of a particular type of imaging system. For example, controller and processing units may include any combination of a motor drive controller, data storage components (such as memory, hard drives, removable storage devices, readers and recorders for media such as CDs, DVDs, and Bluray™ discs), position sensing circuitry and/or software, angle detection circuitry and/or software, timing circuitry and/or software, cardiac gating functionality, volumetric imaging processors, scan converters and others. As noted above, display and user interface 38 is also optionally provided for either real time display or display of data at a time later than the time at which imaging data is acquired.

It is to be understood that patient interface module 36 and controller and processing units 34 are but one example illustration of the selection and organization of hardware subsystems, and that many other implementations are possible. For example, patient interface module 36 may be housed with controller and processing units 34 within processing and display system 49.

Example imaging probe 44 includes an imaging assembly 50, optional imaging conduit 46 along a substantial portion of its length, and connector 48 at its proximal end 47. Imaging assembly 50 is located near distal end 41 of imaging probe 44. Imaging assembly 50 generally refers to the components of the imaging probe 44 from which the signals (either acoustic, optical or both) are collected for the purposes of imaging a region that is proximate to imaging assembly 50. Imaging assembly 50 may house transducers for transmitting and/or receiving imaging radiation. The emitter and receiver may be a single component, as is often the case with a piezoelectric transducer.

In the case of optical imaging, imaging assembly 50 typically contains the distal tip of a fiber optic, as well as a combination of optical components such as a lens (for instance, a ball lens or a GRIN lens). A mirror and/or prism may be included for use in beam delivery and/or collection. Optionally, there may be an optical detector, such as a CCD array, or an optical light source, such as one or more LEDs, incorporated directly in the imaging assembly that may obviate the need for one or more fiber optics in an optical imaging probe.

Imaging probe 44 may contain ports at one or more points along its length to facilitate flushing. Moreover, imaging assembly 50, connector 48 and/or imaging conduit 46 may be filled and/or surrounded with a fluid such as saline, and may be flushed. In applications involving optical imaging, imaging probe 44 may be filled with a gas. The gas may include carbon dioxide or another readily dissolved gas with minimal biotoxicity. Alternatively, in the case of a multimodal optical/acoustic imaging system, imaging assembly 50 may be compartmentalized to include at least one gas-filled compartment or lumen for optical imaging and at least one fluid filled compartment or chamber for acoustic imaging.

Imaging conduit 46 includes at least one conductive wire (optionally two or more) that connect an emitter and/or receiver via connection to an adapter, herein referred to as patient interface module 36. Imaging conduit 46 may include a fiber optic, for example, wrapped by two layers of electrical wire that are electrically insulated from one another. Imaging conduit 46 may further be reinforced by other structural features, such as helically wrapped wires or other designs used to construct imaging torque cables for rotating scan mechanisms. Alternatively, imaging conduit 46 may contain electrical conductors, and a rotational mechanism may be located remote from the proximal end for imparting rotary motion to the imaging assembly. One example mechanism includes a micro-motor and a slip ring in close proximity to the imaging assembly.

The imaging probe 44 may optionally include memory, such as an EEPROM for storing information including calibration information, serial information, probe design information, desired filter information, and any other probe specific information. This memory may reside in connector 48.

Patient interface module 36 facilitates transmission of signals within any fibers and/or wires to the appropriate image processing units. It may contain a motor drive unit for imparting rotational motion to the components of the imaging mechanism.

Additional sensors may be incorporated as part of patient interface module 36, such as position sensing circuitry, for example, to sense the angle of rotation of a rotary component within the imaging probe 44 and/or for detecting the angle of deflection of a member at the distal end 41 of the imaging probe 44. Additionally, patient interface module 36 may include amplifiers to improve the transmission of electrical signals or power between the imaging probe 44 and the rest of the system.

In many applications, it can be important to optimize the geometry of a minimally invasive probe so that it is as small as reasonably possible to achieve its desired purpose. Current IVUS and ICE probes are approximately 0.9 to 4 mm in diameter and the smaller sizes of probes can be delivered more distally within the vascular tree of the coronary anatomy as the vessel caliber tapers down or as diseased vessels are stenosed. Furthermore, within the cardiac anatomy, smaller probes (such as those with a diameter less than about 3.4 mm) can be readily advanced across the atrial septum into the left atrium of the heart. Thus, smaller sizes generally allow for interrogation of a larger portion of the coronary or cardiac anatomy. It is therefore desirable for a probe and its components to be contained within a minimal outer diameter to enable imaging, such as using imaging performed with the scanning mechanisms described by Courtney et al. (US Patent Application Publication No. 20080177138).

FIG. 2a is a perspective drawing of a flexible catheter containing fiber optic 66 and co-axial electrical cable 68. The proximal connector contains fiber optic connection joint 60 that can be received by patient interface module 36 to optically couple imaging fiber optic 66 to image processing and display system 49. Electrical connectors 62 allow one or more electrical conduits to be connected to the ultrasound circuitry and/or controller and processing units. In applications in which the imaging conduit rotates around its longitudinal axis, there may be a need to couple the rotating components of the imaging fiber optic with a relatively stationary fiber optic that connects to image processing and display system 49. This coupling can be achieved with the use of a fiber optic rotary joint incorporated either as part of the proximal connector of imaging probe 48 or as part of patient interface module 36. Similarly, there may need to be a mechanism for coupling the rotating components of the electrical system with relatively stationary electrical components that connect to image processing and display system 49. This can be achieved through the use of one or more electrical slip rings or slip ring channels.

FIG. 2b shows a cross sectional view of the middle section of the catheter shown in FIG. 2a taken along the dotted vertical line. The cross section shows the optional fiber optic 66, optional guidewire 52, imaging conduit lumen 47, external sheath 43, which is a hollow, flexible elongate shaft made of physiologically compatible material and having a diameter suitable to permit insertion of the hollow elongate shaft into bodily lumens and cavities, and co-axial wiring 68. The expanded detailed view of the end of the imaging probe 44 in FIG. 2c shows the imaging assembly 50 which optionally includes a tiltable member 51, distal end of the optional guidewire 52 extended beyond the end of the external sheath 43 and a flush port 53 near the end of the sheath 43. In FIG. 2a, the proximal end of the imaging probe 44 includes an optional guidewire port 56 into which the guidewire 52 is inserted and the connector assembly 48 includes a flush port 58 and electrical contacts 62 along with the connector body. An optional guidewire port 54 is seen in FIG. 2c.

FIGS. 3a-d show an example catheter that employs a tiltable member for scanning an imaging beam. FIG. 3a shows a perspective cutaway drawing of the distal region of an imaging probe 44 that relies on centripetal force to generate the change in tilt angle of the tiltable member 51. Imaging probe 44, which includes a sheath 43 for isolation from bodily fluids and cavities, includes tiltable member 51 housed within imaging assembly 50.

Tiltable member 51 is mounted on pins 102, about which tiltable member 51 is free to pivot. As imaging conduit 46 and assembly 50 (not shown) are rotated about longitudinal axis 59 at a slow rate (indicated by arcing hatched arrow 61), the angle a subtended between longitudinal axis 59 and tiltable member 51 is relatively small. A cutaway perspective cross-sectional view of FIG. 3a is shown in FIG. 3b. FIG. 3c shows a similar drawing of the distal region of imaging probe 44 as shown in FIG. 3a, except with imaging conduit 46 being rotated at a faster rate (indicated by arcing hatched arrow 63) than in FIG. 3a. Centripetal force causes tiltable member 51 to tilt such that there is an increase in the angle a subtended between the longitudinal axis of the catheter and the tiltable member 51. FIG. 3d is a cutaway perspective cross-sectional view from FIG. 3c.

FIG. 3e shows a perspective cutaway drawing of the distal region of a related imaging probe 44 that relies on the use of dynamically controlled magnetic fields to change the deflection angle of tiltable member 51. Imaging probe 44, which may include a sheath 43 for some degree of isolation from bodily fluids and cavities, includes tiltable member 51 comprising part of the imaging assembly 50. Tiltable member 51 is mounted on pins 102, about which the tiltable member 51 is free to pivot. Mounted on the tiltable member 51 is a magnetically influenced element 109 that can be either attracted or repulsed by a magnetic field. For example, it may be a ferromagnetic component, or a permanent magnetic component. Element 109 may integrally be part of tiltable member 51, such as if all or a portion of element 109 is made of either a ferromagnetic or magnetic substrate. An electromagnetic component 107 is also placed at a position separate from the tiltable member 51. The electromagnetic component can be controlled to produce attractive or repulsive forces relative to magnetically influenced component 109. In so doing, the angle a subtended between the longitudinal axis 59 of the catheter and the tiltable member can be adjusted as desired. Furthermore, similar imaging probes may be conceived that involve interchanging the position of the electromagnetic component 107 and magnetically influenced component 109, or using two electromagnets instead of an electromagnet and a magnetically influenced component. A cutaway perspective cross-sectional view of FIG. 3e is shown in FIG. 3f.

FIG. 3g shows a similar drawing of the distal region of imaging probe 44 as shown in FIG. 3e, except with a repulsive sequence applied to electromagnet 107 such that the angle a subtended by tiltable member 51 is increased. FIG. 3h is a cutaway perspective cross-sectional view from FIG. 3g.

Tiltable member 51 may be an ultrasonic transducer, such as an ultrasound transducer used for producing B-scan ultrasound images. Another embodiment includes an ultrasound transducer mounted on a tiltable member.

Figure 3I:
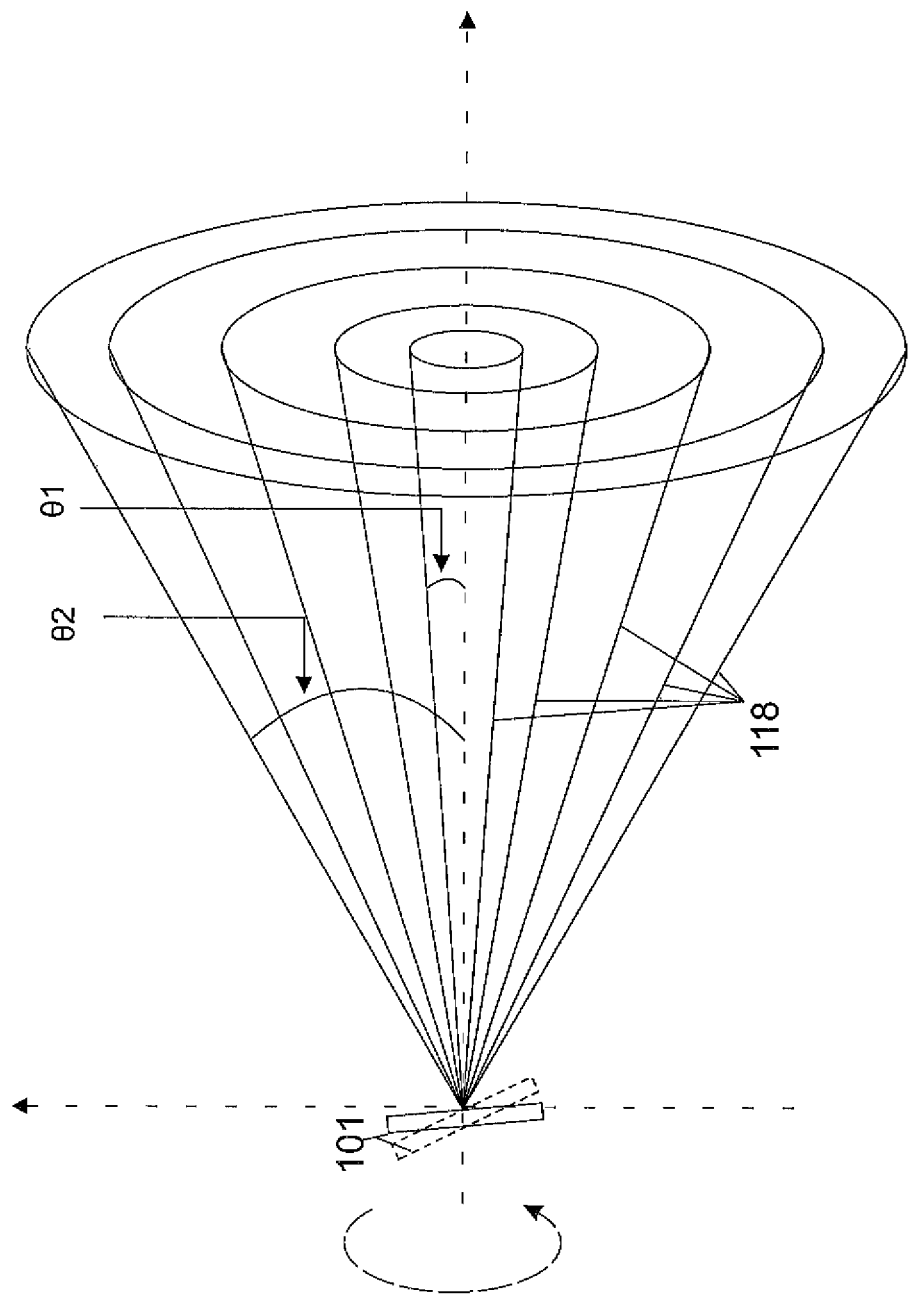
FIG. 3i shows a potential scanning pattern for generating 3D images with imaging angle information.

FIG. 3i shows an example of a potential scanning pattern for generating ultrasound images. In this case, the tiltable member is an ultrasound imaging transducer 101. As imaging conduit 46 and assembly 50 are rotated at a constant rate, an image is generated along a surface that approximates a cone. As the rate of rotation is changed, centripetal force causes the angle subtended between the longitudinal axis of the catheter and ultrasound imaging transducer 101 to change resulting in a series of concentric imaging cones 118 for different rotational speeds. The angle subtended between the longitudinal axis of the catheter and an axis normal to ultrasonic imaging transducer 101 will be referred to as the "imaging angle". In this case, the transducer begins with a relatively small imaging angle θ1 implying a fast rate of rotational speed. As the rotational speed is reduced, the imaging angle is increased to θ2.

Figure 3J:
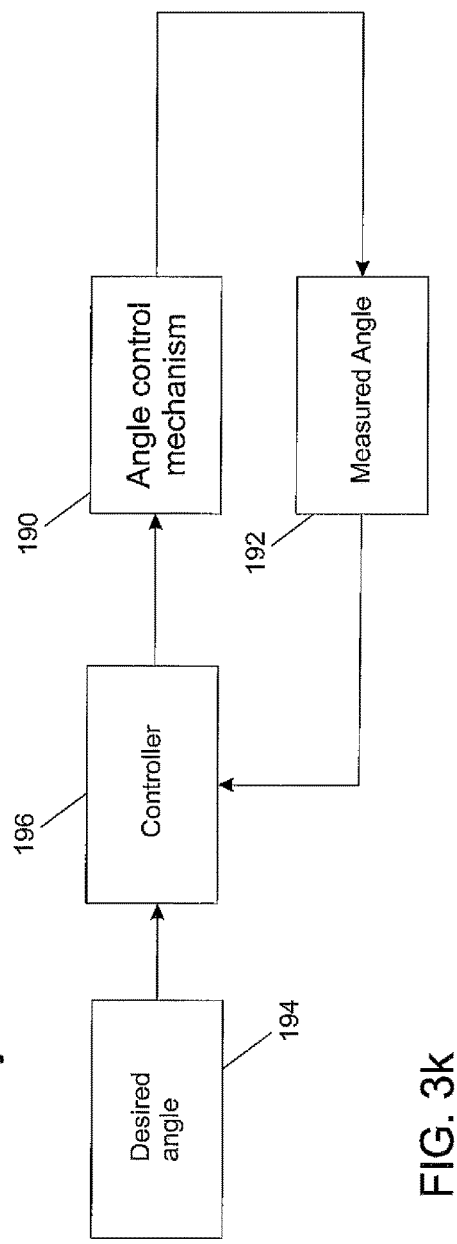
FIG. 3j illustrates a control system in which the angle sensing transducer is employed to provide feedback for controlling a direction of the emitted imaging beam.
Figure 3K:
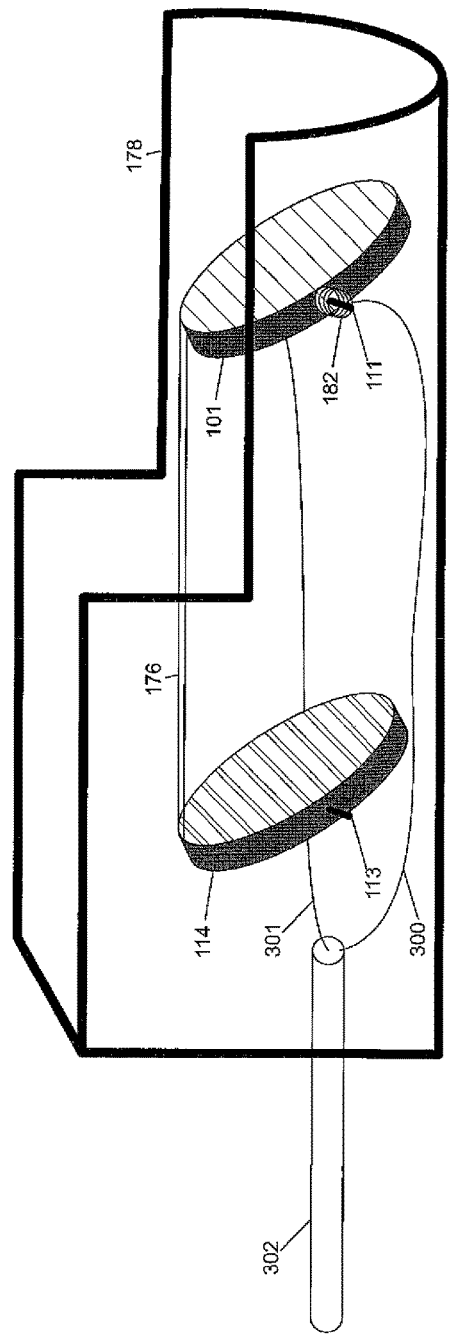
FIG. 3k shows an implementation of a system using a torsional spring as a restoring mechanism.

In order to cause the imaging angle to return to a stable position in the absence of rotation, a restoring mechanism can be used as shown in FIG. 3k. Here, the primary movable member 101 is connected to a secondary movable member 114 using a mechanical coupler 176, allowing the two members 101 and 114 to move synchronously. All components are housed within a shell 178. One or more springs 182 are connected between the movable member 101 and the shell 178. The springs may be torsion springs, linear springs, or a cantilever spring. The movable members 101 and 114 are pivotally supported by around pins 111 and 113 respectively. This spring 182 provides a force to restore the member 101 to the side viewing position in the absence of adequate rotational force to overcome the restoring force provided by spring 182. In addition to adding a mechanical restoring force, the torsional springs may also be formed, at least in part, from an electrically conductive material, such as stainless steel, beryllium copper, copper, silver, titanium, gold, platinum, palladium, rhenium, tungsten, nickel, cobalt, alloys that include one or more of these metals and many other metals and their alloys can be used to provide electrical connections. Here, spring 182 is in electrical communication with conductor 300. Conductor 301 makes a similar connection to the opposite side of movable member 101 (not shown).

Alternatively a spring that provides both a restoring force and an electrical connection may be made of more than one material, where one material provides conductive properties and another material provides mechanical properties for the restoring force. For example, a torsion spring may be formed of a nitinol core with a gold outer layer, applied by sputtering, plating, evaporation, electroforming, electroplating, electron beam techniques or other methods known in the art. Alternatively, one or more of the materials may be a material other than a metal, such as a polymer.

The conducting elements of the spring have cross sectional dimensions on a micron scale (for example, less than about 100 microns×100 microns) using photolithography and related techniques. Gold hardened with cobalt and nickel cobalt provide further examples of suitable materials for a conductive spring with desired mechanical properties. A portion of the surface of the spring may be covered by an insulating material, such as parylene, Teflon, polyimide and many others. Alternatively, the insulating may occur by processing the outer surface of the spring, such as by allowing an oxide to form on the outer surface of a metal or alloy.

Example embodiments described below provide ultrasonic apparatuses and methods for combining multiple ultrasound transducers on a single electrical channel. One application that will be described in detail relates to the fact that in order to accurately reconstruct a 3D image of the imaging field, the imaging angle must be determined for a given ultrasound image acquisition event, vector, or pixel. As noted above, while the proceeding embodiments relate to applications involving minimally invasive imaging, where angular detection is performed using an apparatus mounted within an imaging assembly within an imaging probe, it is to be understood that these applications are merely non-limiting examples that are provided for teaching purposes and are not intended to limit the scope of the disclosed embodiments.

Referring now to FIGS. 4a-g, an ultrasonic angle detection apparatus is shown for detecting a change in angle of a tiltable member using a time of flight detection method. Angle detection transducer 100 is placed at a fixed location relative to an initial position of tiltable member 101, which includes material that is at least partially acoustically reflective relative to the acoustic transmission medium. Angle detection transducer 100 transmits ultrasonic beam 110 towards the tiltable member 101. As the beam reaches the tiltable member 101, a portion of the beam is reflected back towards the angle detection transducer 100. The acoustically reflective substrate may be configured to reflect or scatter components of the incident ultrasonic beam in a diffuse manner, as will be described in further detail below.

Tiltable member 101 may itself be acoustically reflective, or may have attached to one or more of its surfaces, such as its back surface, an acoustically reflective substrate. As noted above, acoustic reflections may be diffuse to support the detection of a reflected ultrasonic beam over a broad range of tilt angles (or imaging angles), and the reflected ultrasonic beam may be generated by surface reflection, volume reflection, or a combination thereof. In an example embodiment, tiltable member 101 includes an imaging transducer that transmits an acoustic beam 120 in a direction away from the angle detection transducer 100. It is not necessary that the angle detection mechanism only uses the back surface of the tiltable member. It may be oriented and/or positioned to use any side or surface of the tiltable member as best suited for any particular embodiment.

Figure 4B:
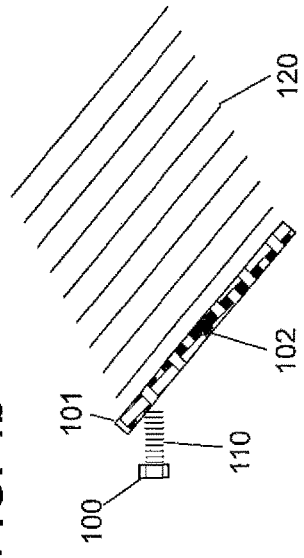
FIGS. 4a-e demonstrate the use of a high frequency ultrasound transducer to estimate the tilt angle of a tiltable ultrasound transducer using a time of flight method.
Figure 4A:
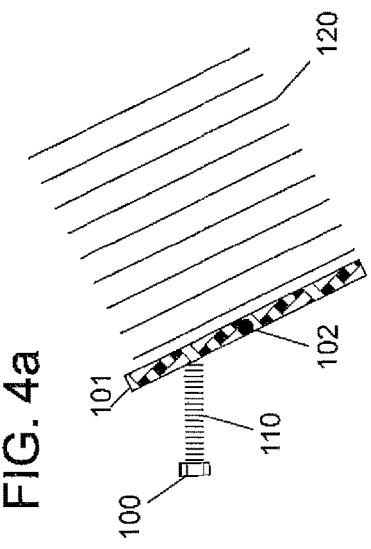
Figure 4E:
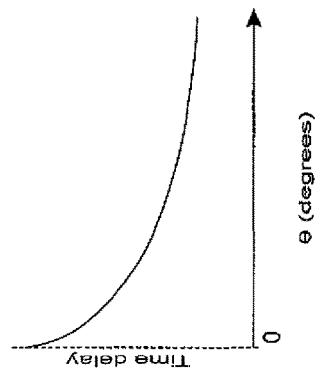

FIGS. 4a and 4b show two different angular positions of tiltable member 101, which is rotatable about pivot axis 102. In one example embodiment, the pivot axis is implemented using or more pins or a hinge aligned along the pivot axis around which the tiltable member pivots. In FIG. 4a, the separation between tiltable member 101 and angle detection transducer 100 is greater than in FIG. 4b. This separation distance results in the angle detection beam 110 having a shorter time of flight in FIG. 4b than FIG. 4a.

The tilt angle can be calculated with the time of flight and prior knowledge of the geometric configuration of the transducer and the tiltable component, including their relative locations in space and ranges of motion, and the speed of sound in the acoustic path. The acoustic beam for the angle detection transducer may travel through a medium such as water or saline, wherein the speed of sound is approximately 1450 to 1600 m/s.

For example, if the angle is to be determined based on differences in time of flight, a baseline signal may be captured at a known angular position and known estimated time of flight during an initialization phase. This baseline signal may be used as a comparator against signals received at different positions to estimate tilt angle using the techniques described above.

Alternatively, the tilt angle can be determined empirically based on calibration measurements made with known angular deflections. Calibration measurements can be employed to produce a calibration curve, such as the curve shown in FIG. 4e. Such calibration data may be stored in an EEPROM provided within the imaging probe, as described above.

Figure 4D:
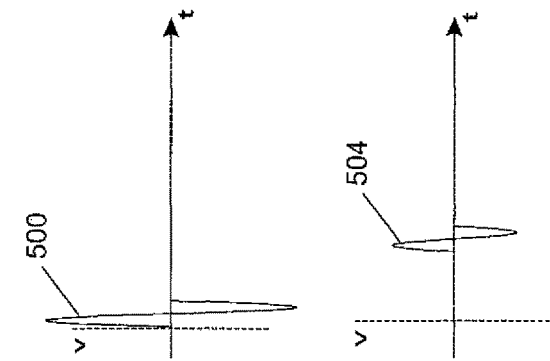
Figure 4C:
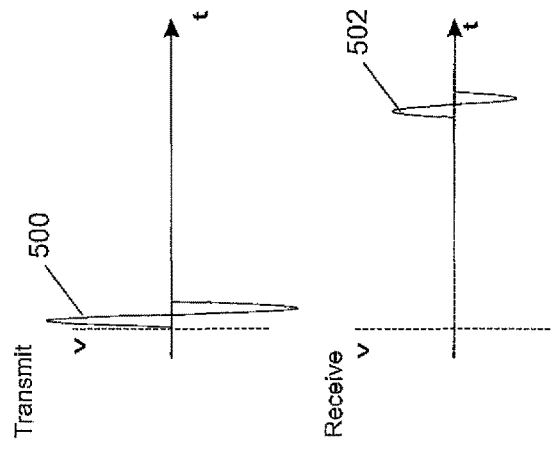

FIGS. 4c and 4d are timing diagrams that represent the signal detected for each angle scenario in FIGS. 4a and 4b, respectively. In these examples, a pulse 500 is transmitted from transducer 100 at time (t)=0 and a received pulse is detected at a later time with a reduced magnitude. The received pulse 502 corresponding to the signal reflected from tiltable member 101, as oriented in FIG. 4a, has a greater time delay than the received pulse 504 corresponding to the signal reflected from tiltable member 101 in FIG. 4b. Furthermore, as acoustic waves propagate through a medium, they are partially attenuated. This attenuation is frequency dependent with energy components in the higher frequencies attenuated more than lower frequency energy components. As a result of this, not only is the delay between received pulses changed, so too is the spectral content of the received pulse 504. In this embodiment, a change in spectral content can also be related to the tilt angle.

The tilt angle determined using the above method may be employed for feedback in a control system, as shown in FIG. 3j. A desired angle 194 and the measured angle 192 (determined using the aforementioned method) are provided as inputs to controller 196, and the output of controller 196 is provided to angle control mechanism 190. A variety of control methods and algorithms known in the art may be employed, including, but not limited to, PID and fuzzy logic controllers.

In another example embodiment, the tiltable member is employed to direct a beam of ultrasonic radiation from an imaging ultrasonic transducer housed within an imaging probe, where the ultrasonic imaging transducer and the angle sensing transducer are electrically connected to a common channel for excitation and detection. The ultrasonic imaging transducer may form tiltable member 101, or alternatively may be mounted to tiltable member 101, or may be fixed relative to tiltable member 101 such that the imaging beam is reflected, scattered, and/or refracted by tiltable member 101 (as shown in embodiments described below).

By connecting both transducers to a common electrical channel, a simple, reliable, cost-effective, and space efficient system is realized. Furthermore, the ability to use a common electrical channel may minimize the number of electrical connections that need to be made. For example, if the electrical connections to an ultrasound imaging transducer mounted on or incorporated as tiltable member 101 are via wires or conductive springs from the housing of imaging assembly 50 to tiltable member, the wires or springs will mechanically influence the ease with which tiltable member can tilt. It may be desirable to minimize the number of wires or springs between tiltable member 101 and the rest of the imaging assembly 50.

Using a common electrical channel for both an imaging transducer and an angle detection transducer reduces the number of electrical conductors to the tiltable member and may thus provide more flexibility in the design and/or performance of the imaging probe. Similarly, using a common electrical channel may reduce the number of channels that need to be accommodated by the patient interface module 36 (the patient interface module contains components, such as slip rings, that couple electrical signals between the rotating parts of the imaging probe and the non-rotating parts of the image processing and display system 49). Similarly, using a common electrical channel may reduce the number of analog to digital converters or reduce the number or complexity of other signal processing components in the image processing and display system 49.

Furthermore, a common electrical channel may help optimize the size, configuration and/or number of electrical conductors in the imaging conduit. This would potentially improve the mechanical properties of the imaging conduit 46, such as improving the flexibility of the imaging conduit, reducing the amount of non-uniform rotational distortion, reducing the required size of the imaging conduit 46 or providing room for additional features to be incorporated into imaging probe 44.

It is to be understood that the present embodiments pertaining to the connection of two or more ultrasonic transducers on a common electrical channel are not intended to be limited to applications involving the use of one imaging transducer and one angle detection transducer. As further described below, the common electrical connection of multiple ultrasonic transducers within a longitudinal body of an ultrasonic probe may be implemented in a wide variety of applications, for which imaging and angle detection are illustrative yet non-limiting embodiments.

FIGS. 5a and 5b provide schematics illustrating two example embodiments in which a single electrical channel is employed within imaging conduit 46 as a source for both an imaging transducer 105 in the imaging probe 44 and a second transducer, such as an angle detection transducer 100.

FIG. 5a shows the distal end of coaxial cable 302, where first and second conductive paths 300 and 301 are connected in parallel to ultrasonic imaging transducer 105 and ultrasonic angle detecting transducer 100. For minimally invasive imaging procedures, electrical cable 302 may be a micro-coaxial cable or micro twisted pair with a diameter of less than about 1000 microns, or alternatively less than 500 microns. Excitation pulses are transmitted to both ultrasonic transducers along signal wire 301, while a second connection, optionally to ground, is provided by second wire 300. The conductive paths of the channel, labeled as the signal (+) and ground (GND) paths may be interchanged. Both transducers are shown in a side view.

Imaging transducer 105 may be larger in size than angle sensing transducer 100, and imaging transducer 105 may possess a lower center frequency than angle sensing transducer 100. In one example implementation, the center frequency of imaging transducer 105 may be in the range of 5-60 MHz, while the center frequency of angle detection transducer 100 may be in the range of 25-100 MHz. In another example embodiment, the transducers differ in center frequency by a factor of at least about 2.5. In one embodiment, the factor is between about 2.5 and 3. In one specific and non-limiting example, one transducer may have a center frequency of 15 MHz, and the other transducer may have a center frequency greater than about 40 MHz.

Imaging transducer 105 generally consists of a piezoelectric material 319, commonly PZT-5H, but may include other piezoelectric ceramics, a composite design, a single crystal design, lithium niobate, PVDF and a variety of other materials known for ultrasound transducer fabrication, including cMUT and pMUT transducers. The piezoelectric is coated on both sides 318 and 320 with conductive layers, such as thin layers of gold or other materials with high conductivity. On one side of the piezoelectric layer 319, a backing layer 321 may be applied to dampen undesired acoustic signals from going through the back of the transducer. The backing layer 321 may be electrically conductive, as this simplifies an electrical connection with angle detection transducer 100, as will become apparent below. In an alternative embodiment in which the entire backing layer 321 and/or backing layer 310 is not electrically conductive, suitable electrically connections between signal wire 301, conductive layer 320, and conductive layer 311, may be provided through a conductive channel formed within backing layer 321 and/or backing layer 310 or through a conductive wire connecting the conductive regions. The signal conduction wire 301 is connected electrically to conductive layer 320, such as through a conductive backing layer 321. Alternatively, other conductive paths between signal conduction wire 301 and conductive layer 320 can be used. In the example embodiment of FIG. 5a, all regions sharing the electrical connection to the signal conduction wire 301 are labeled with a "+" symbol. At one end of the transducer backing layer 321, an electrically insulating barrier 331 is bonded to the transducer. On the face of the piezoelectric material 318 opposite the backing layer 321, a thin layer of an electrically conductive acoustic impedance matching material 317 is bonded.

A thin and electrically conductive layer 316 is bonded adjacent to the electrically insulated barrier 331. Ground connection 300 is connected electrically to this layer. All regions sharing the electrical connection to the ground conduction wire 300 are labeled as "GND". The acoustic beam emitted from the imaging transducer is directed along an axis normal to the transducer surface 392.

Similar to the design of the imaging transducer 105, angle detection transducer 100 consists of a piezoelectric material 312, commonly PZT-5H, but may often include a composite design, a single crystal, lithium niobate, or PVDF and a variety of other materials known in the art. Piezoelectric layer 312 is coated on both sides 311 and 313 with a thin conductive layer, commonly gold. On one side of piezoelectric layer 312, a backing layer 310 is applied to damp out undesired acoustic signals from going through the back of the transducer. Backing layer 310 may be electrically conductive and electrically connected to backing layer 321. At one end of the transducer backing complex, a thin electrically insulated barrier 330 is bonded to the transducer. On the face of the piezoelectric material 312 opposite backing layer 310, a thin layer of an electrically conductive acoustic impedance matching material 314 is bonded. A thin electrically conductive layer 315 is bonded adjacent to the electrically insulated barrier 330. The acoustic beam emitted from angle detecting transducer 100 is directed along an axis normal to the transducer surface 394. Alternatively, backing layer 310 may be omitted and conductive layer 311 may be directly bonded to backing layer 321. In this case, the two transducers may share backing layer 321 for damping out unwanted acoustic signals.

In order for the transducers to share electrical connections in an embodiment in which the transducers form a unitary structure, they may be mounted or bonded such that the conductive ground channels 315 and 316 of each transducer are in direct electrical contact, the electrically insulating barriers 330 and 331 are in continuity, and the backing layers 310 and 321 of both transducers are electrically conductive and in direct contact with each other. There should be high electrical resistance between the electrically conductive signal regions and ground regions of either transducer in order to maintain appropriate connections.

It is to be understood that the embodiment described in FIG. 5a is example of one of several embodiments wherein two ultrasound transducers can share a single electrical channel and form a unitary structure. In an alternative embodiment, one or more of the backing layers need not be electrically conductive, provided that conductive pathways to opposing sides of piezoelectric elements 312 and 319 for each of the transducers are provided. Electrically conductive pathways can be made using materials such as wires, metals, conductive epoxies and other materials known in the art. The pathways may be made using processes such as, but not limited to, layering, bonding, and soldering, sputtering, wire bonding.

Acoustic matching layers 314 and 317 may improve the efficiency of acousto-electric coupling but may not be necessary for one or more of the transducers. In an alternative embodiment, a plurality of matching layers may be used for one or more of the transducers. Furthermore, electrically insulating barriers 330 and 331 provide example embodiments for electrically isolating the signal and ground pathways from each other but may take on more complex arrangements than described in FIG. 5a, and may include a void or gap made of an insulating gas or liquid rather than a solid material. Furthermore, the signal and ground designations of each side of the two transducers are arbitrary and can be connected in several permutations of arrangements.

FIG. 5b illustrates an embodiment for sharing a single electrical connection between the angle detection transducer 100 and imaging transducer 105 while the two transducers do not form a unitary structure. For example, the transducers may be fabricated in the same way as described in reference to FIG. 5a, but are not bonded together. Instead, the signal connection 301 and ground connection 300 from coaxial cable 302 are connected electrically to opposing sides of the piezoelectric elements 313 and 319 both the angle detection transducer 100 and the imaging transducer 105. In the example shown in FIG. 5b, all regions sharing the electrical connection to the signal conduction wire 301 are labeled with a "+" symbol. Similarly, the ground connection 300 is connected electrically to both the conductive path 315 on the angle detection transducer 100 and the conductive path 316 on the imaging transducer 105. All regions sharing the electrical connection to the ground conduction wire 300 are labeled as "GND" in FIG. 5b. In one example embodiment, the ultrasound transducers operate at substantially different center frequencies.

In some embodiments, a multi-transducer imaging probe is provided in which the imaging probe houses two or more ultrasonic imaging transducers that are connected to a common electrical channel. Each transducer may be selected to exhibit a unique spectral response that is substantially spectrally distinct and non-overlapping from the other ultrasonic transducers. As noted above, additional electrical filtering may be employed to provide additional spectral isolation among the ultrasonic transducers.

The imaging transducers may be positioned to direct each ultrasonic imaging beam in a distinct direction, thereby enabling simultaneous imaging at multiple angles. Unlike phased array imaging, in which multiple ultrasonic transducers are driven in a phased relationship by unique and individual electrical channels, the present embodiment enables multi-transducer, multi-angle and/or multi-frequency imaging based using a single electrical channel upon which the signals for exciting the different transducers are multiplexed.

In one example embodiment, two or more imaging transducers may be oriented to direct their ultrasonic imaging beams in a substantially common direction, which may be useful, for example, for simultaneous imaging in multiple acoustic spectral windows. In other embodiments, as shown below, three or more transducers can be used to form unitary structures similar to those shown in FIGS. 5c and 5d, and that multiple transducers can be oriented at arbitrary angles with respect to each other.

Figure 5C:
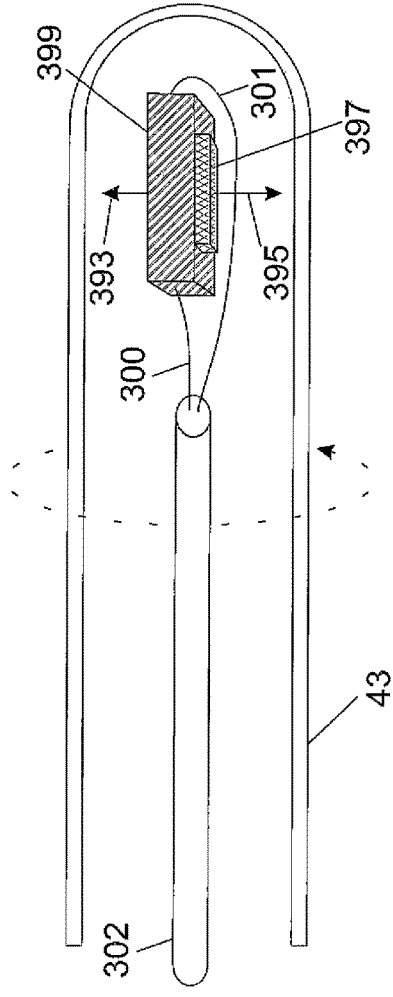
Figure 5D:
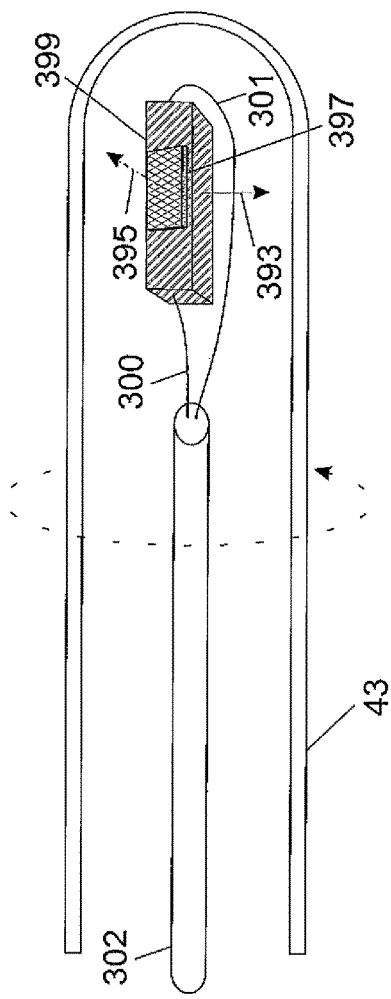

FIGS. 5c and 5d show two example embodiments in which an imaging probe houses two imaging transducers oriented with a relative angle of 180° and 90°, respectively.

Transducers 399 and 397 are electrically connected via common coaxial conductor 302 (comprising common ground wire 300 and common signal wire 301), and are shown as housed within sheath 43. Connections to the suitable conductive layers of transducers 397 and 399 may be made, for example, as shown in FIG. 5a. It should be noted that conductive paths within the unitary structure can be configured such that conductive paths 300 to 301 connect to a common side of the unitary structure, or in various other arrangements such that the electrical connections within the unitary structure provide appropriate conductive paths to transducers 397 and 399. In other example implementations, the connections to the conductive layers of the transducers may be made, as described above, using materials such as wires, metals, conductive epoxies and other materials known in the art, and pathways may be made using processes such as, but not limited to, layering, bonding, soldering, sputtering, wire bonding.

FIG. 5c demonstrates a catheter housed in a sheath 43 configured for side-viewing imaging with a unitary structure formed by joining ultrasound transducers 397 and 399. Here, transducers 397 and 399 transmit anti-collinear beams, 393 and 395 respectively, in a generally side viewing direction relative to the longitudinal axis of the catheter. Upon a complete revolution of the distal imaging assembly, both transducers will have imaged the same region in tissue. This arrangement may be useful in a situation where it is desired to image the same region of tissue with two different frequencies, often a low frequency for deep penetration and a higher frequency to achieve high resolution. While this embodiment shows beams 393 and 395 being anti-collinear, other useful embodiments would include beams that are anti-parallel, but not necessarily anti-collinear.

Similarly, FIG. 5d shows an example implementation in which ultrasound imaging transducers 397 and 399 are both in a generally side viewing direction while transmitting substantially orthogonally directed beams with the centers of the transducer apertures positioned at approximately the same position along the probe's longitudinal axis. Upon a complete revolution of the distal imaging assembly, both transducers will have imaged the same region in tissue.

FIGS. 5c and 5d provide two non-limiting embodiments of imaging probes housing dual transducers that are electrically addressable via a common electrical channel, for which many other related embodiments and design variations are possible. For example, any of the embodiments of the present disclosure involving tiltable, pivotable, rotatable and movable elements for directing an emitted imaging beam may be adapted to further include a second imaging transducer according to the present embodiment, where the second imaging transducer need not necessarily be physically contacted with the first imaging transducer.

In some embodiments, the second imaging transducer may be positioned or oriented to have a field of view remote from the first imaging transducer. Alternatively, the first and second imaging transducers may have fields of view that overlap to create a combined field of view, wherein the signals from one transducer may be used to provide ultrasound data for one portion of the combined field of view and signals from the second transducer are preferentially used to provide ultrasound data for another portion of the combined field of view. Ultrasound data from each of the one or more transducers may be used for any of several purposes, including imaging, tissue characterization, sensing of instruments outside the imaging probe, and sensing movement of components within the image probe.

For example, in the embodiments shown in FIGS. 5c and 5d, a transducer with a first center frequency may be used for imaging more distant regions in the combined field of view, while a second transducer with a lower center frequency than the first transducer may be used for providing higher resolution imaging data in regions closer to the imaging catheter. Furthermore, such embodiments may optionally include one or more angle sensing ultrasonic transducers for detecting the direction of an ultrasonic imaging beam emitted by the first and/or second imaging transducers, where the angle sensing transducers are also connected to the common electrical channel.

FIG. 5e shows a scenario where one imaging transducer 387 is shaped such that it contains features that allow for the mounting of a second transducer 397 at an oblique angle relative to the longitudinal axis of the imaging probe. When the distal imaging assembly is rotated, transducer 387 will image a largely side-viewing region of tissue, while transducer 397 will image a partially forward viewing conical region of tissue.

FIG. 5f shows a configuration of a unitary structure of multiple ultrasound transducers driven on a single channel suitable for situations where multiple collinear imaging beams are desired. In the embodiment show in the Figure, a lower-frequency beam 389 is transmitted from transducer 391 in parallel with a higher-frequency beam 392 from transducer 397. Transducer 397 also receives corresponding echoes.

The embodiment shown in FIG. 5f may be employed for second order ultrasound field (SURF) imaging. SURF imaging uses acoustic energy in two distinct frequency bands transmitted simultaneously. The energy in one frequency band is generally at a low frequency (a center frequency in the range of 0.5-10 MHz) and is used as a modulation or manipulation pulse. The energy in the high frequency band tends to be centered approximately 7-10 times higher than the center frequency of the low frequency band. The high frequency energy band is employed to image the tissue under different modulation pressures, as generated but the modulation or manipulation pulse. Accordingly, referring to FIG. 5f, ultrasound transducer 397 may be employed to provide a high frequency imaging beam, while larger ultrasound transducer 391 may be provided to generate a SURF ultrasound beam that is parallel and substantially collinear to the imaging beam. While this technique has been performed with two separate ultrasound transducers with two separate electrical channels, the present embodiment may be performed to achieve SURF imaging with a single electrical channel.

Figures 5G, 5H:
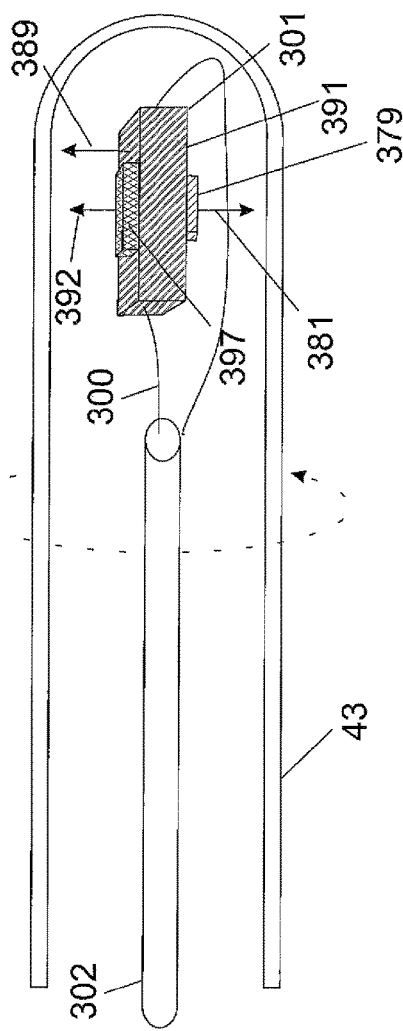
FIG. 5g shows a three-frequency imaging arrangement.
FIG. 5h shows an arrangement with a two-frequency assembly combined with an optical imaging modality.

It may also be desirable to include more than two imaging transducers on the same unitary structure connected by a single electrical channel. FIG. 5g shows a configuration including three ultrasound transducers, each of which is characterized by a different center frequency. An example of an application for such an embodiment is again for SURF imaging. A low frequency manipulating beam 389 is transmitted from transducer 391 and used to modulate tissue being imaged, while a higher frequency imaging beam 392 is emitted from transducer 397 in a direction that is collinear to modulating beam 389. Positioned to create an antiparallel, and, in some embodiment, anti-collinear, beam 381 is another transducer 379. The frequency of beam 381 may be selected to be higher than that of imaging beam 392 to provide high resolution imaging. One example of a suitable set of frequencies is a 3 MHz modulating beam 389, a 25 MHz SURF imaging beam 392, and a 60 MHz high frequency imaging beam 381.

It may also be desirable to combine multi-frequency transducers with other imaging modalities. One potential family of modalities is fiber compatible optical imaging modalities. These may include optical coherence tomography, fluorescence imaging, photoacoustic imaging, angioscopy, Raman spectroscopy and other optical modalities known in the art. FIG. 5h shows one such configuration including a unitary structure having three components: (1) an ultrasound transducer 399 having a first center frequency, (2) a second ultrasound transducer 397 having a second center frequency that is different from the first center frequency, with both ultrasonic transducers connected to a common electrical channel, and (3) an optical imaging system 383 configured to generate optical imaging beam 385. In the example embodiment shown in the Figure, the second ultrasound transducer 397 contains a hole and an optical beam director to allow optical imaging beam 385 to emerge substantially collinear with second ultrasound imaging beam 395.

While the imaging transducers shown in FIGS. 5a-h are shown as flat transducers, one or more of them may be curved to provide beam focusing. In many applications, it may be beneficial to provide a focused ultrasound beam, or beams, for improved lateral resolution at a desired depth. It may specifically be desirable to focus higher frequency ultrasound beams at regions of interest that are closer to the imaging assembly, and to focus lower frequency ultrasound beams at regions of interest further from the imaging assembly. This enables lateral resolution high resolution images at multiple depths, giving an effectively improved depth of field. In this case, the highest lateral resolution would be achieved close to the imaging probe, where it is often desired for a number of imaging or image guided procedures such as crossing CTOs, vulnerable plaque detection, or transseptal puncture. An embodiment showing focused transducers is shown in FIG. 5i, where a first, low frequency transducer 373 is curved to focus at a depth 375 with acoustic beam 374. A second, high frequency transducer 376 has its acoustic beam 377 focused to a depth 378, which is closer to the imaging probe than 375. There are multiple ways of achieving focus on an ultrasound transducer, including using acoustic lenses, mechanical pressing, machining of a curved surface, or using a flexible piezoelectric such as PVDF or a composite material that can be formed into a curved surface.

As noted above, in some example embodiments, excitation pulses and detected signals are respectively transmitted to and received from both transducers on a common electrical channel, while enabling the detected signals from each transducer to be separated or demultiplexed for image processing and/or angle determination. There are numerous techniques that can achieve this without departing from the scope of the present embodiment. Selected techniques involve separating the frequency spectra of the imaging signal information and the angle detection signal information.

One embodiment for demultiplexing both detected signals is illustrated in FIG. 6. The center frequencies of both transducers are selected such that there is substantially little or no overlap between the respective transducer spectral bandwidth ranges 396 and 398. If the transducers are adequately separated in terms of frequency spectra, signals from one transducer will not interfere with signals from the other. That is, in the illustrative context of an embodiment involving an imaging transducer 105 and an angle detection transducer 100, an imaging pulse sent to the imaging transducer 105 will not cause a significant acoustic response from the angle detection transducer 100.

Common definitions of spectral bandwidth in ultrasound are based on the range of frequencies surrounding a peak amplitude of the frequency domain representation of an acoustic or electrical signal generated or detected by an ultrasound transducer. In one embodiment, the spectral bandwidths are at least 6 dB bandwidths. For example, the 6 dB spectral bandwidth typically refers to the range of frequencies surrounding a frequency of a peak amplitude in which the amplitude of the signal across that range of frequencies is within 6 dB of the peak amplitude. The 20 dB and 40 dB spectral bandwidths are also commonly used. An example frequency spectrum 396 of imaging transducer 105 and an example frequency spectrum 398 of angle detection transducer 100 are plotted in FIG. 6 such that the 6 dB points of both transducers intersect with the x-axis. Similarly, an angle detection pulse sent to the angle detection transducer 100 will not cause a significant acoustic response from the imaging transducer 105.

The frequencies of the two transducers may be selected to avoid harmonics of the transducer center frequencies. In general, it may be advantageous to avoid having the center frequencies of the transducers as integral multiples of one another, so as to avoid confusion caused by harmonics from non-linear echoes. This is especially true for cases where microbubble specific imaging techniques are being used, as many of these techniques rely on harmonics for separation between tissue and contrast agent. The higher frequency transducer may be configured to have a larger absolute bandwidth to take advantage of increased axial resolution at the higher frequency, as shown.

In some circumstances, imaging excitation pulses may possess a significantly broader bandwidth than that of the imaging transducer, thereby resulting in the possibility of transmitted pulses spectrally overlapping with the bands of both transducers. This may be mitigated using analog or digital filtering techniques to separate the effective bands of the excitation pulses received by the individual transducers.

Figure 7:
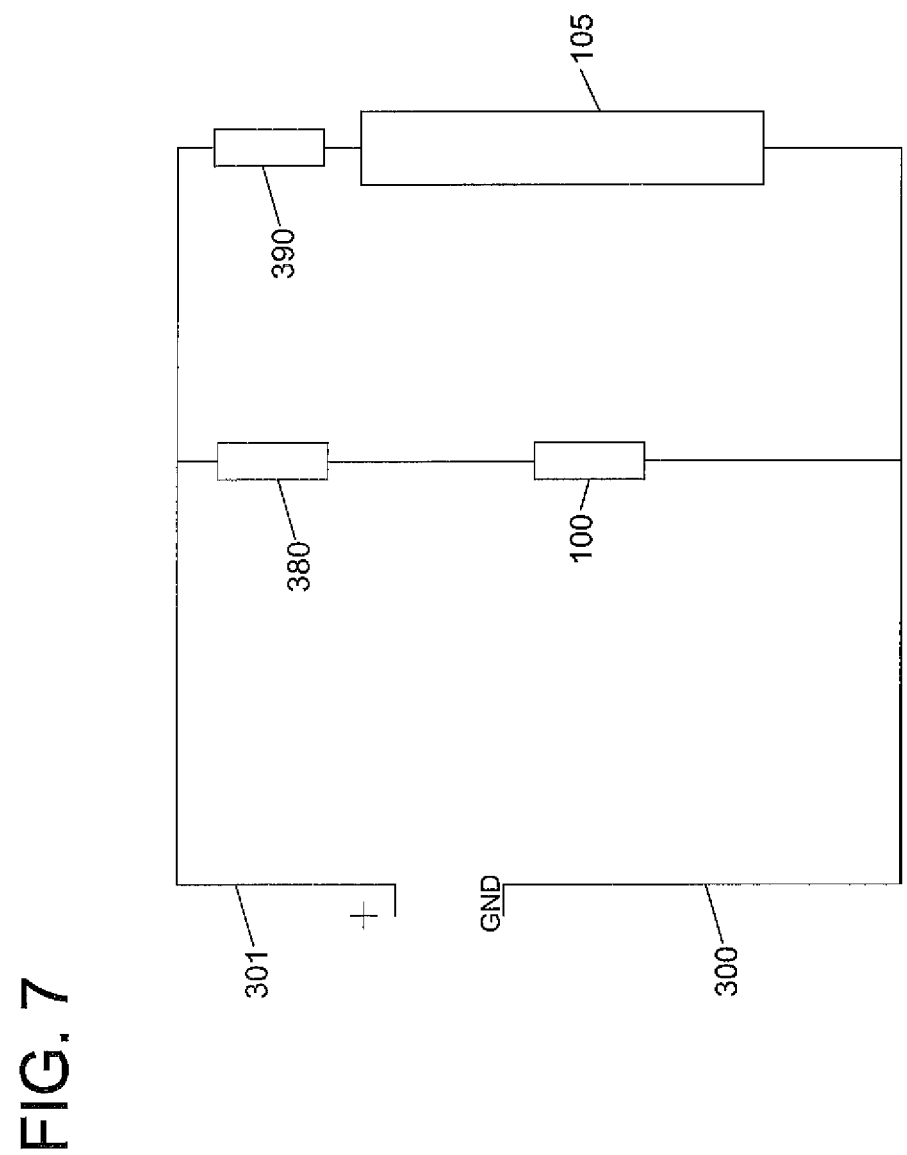
FIG. 7 shows the use of tuning elements for the two ultrasound transducers using separate RLC circuits for each of the transducers.

In one embodiment, such a filtering scheme may be implemented using passive elements as shown in FIG. 7. A filter 380 may be generated from a combination of electrical components, such as resistive, inductive and/or capacitive components, and is employed to spectrally restrict imaging pulses from exciting the angle detection transducer 100, while a filter 390 may be generated from a combination of electrical components to spectrally restrict angle detection pulses from exciting the imaging transducer 105. Alternatively, narrower band excitation pulses can be used for imaging, angle detection or both.

In another example embodiment, in which both transducers are spectrally isolated as shown in FIG. 6, a broadband excitation pulse or waveform may be provided that overlaps the spectral bandwidths of both transducers, or the excitation waveform may include a first spectral component that is within the bandwidth of one transducer, and a second spectral component that is within the bandwidth of another transducer.

Detected signals are demultiplexed in the frequency domain using spectral filtering techniques to individually resolve the signals detected from each transducer. Spectral filtering of the detected signals may be implemented using either analog or digital filtering, or both. For example, the signal from the single electrical channel can be separated using analog filters to two separate receive channels that may be connected to two separate analog to digital converters in image processing and display system 49. Alternatively, digital spectral filtering can occur on digitally sampled representation of the received signal using a single analog to digital converter where digital processing hardware or software, are used to separate the imaging and angle detection data.

FIGS. 8a-e illustrate an embodiment in which tiltable member 150 is configured to reflect incident radiation from imaging transducer 105, and where the angular deflection of tiltable member 150 is detected using a time of flight method. In this case, imaging transducer 105 is mounted at a fixed location and oriented towards the tiltable member 150.

As shown in the figure, another imaging transducer or imaging radiation source 103 can be mounted adjacent to, attached to, or transmitting through a hole bored into the imaging transducer 105 as described in US Patent Publication No. 20080177183. For example, an optical imaging source/receiver 103 could be mounted to ultrasound imaging transducer 105 to provide a second imaging modality within an imaging probe. It is to be understood that it is not necessary that the front surface of reflective tiltable member 150 is the same as the back surface of the reflector 153. The front surface 151 may be constrained to being highly optically and/or acoustically reflective, while it may be desirable for the back surface 153 to be a diffuse acoustic reflector and/or scatterer.

Figure 8A:
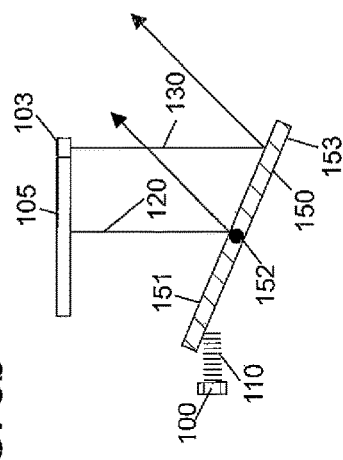
FIGS. 8a-8e demonstrates the use of a high frequency ultrasound transducer to estimate the deflection of a tiltable optical and/or acoustic mirror.
Figure 8B:
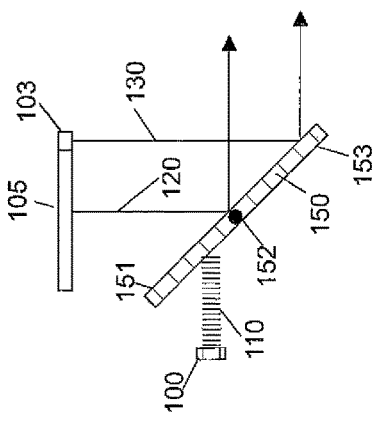

FIGS. 8a and 8b illustrate a common embodiment with tiltable member 150 shown at two different tilt angles, where tiltable member 150 is rotatably mounted on pivot axis 152. Angle detection transducer 100 is placed at a fixed location relative to pivot axis 152. Imaging transducer 105 transmits an acoustic beam 120, while optical imaging source 103 transmits an optical beam 130, where both acoustic beam 120 and optical beam 130 are transmitted in a direction towards the front surface 151. Angle detection transducer 100 transmits an acoustic beam 110 towards the back surface 153 of tiltable member 150, and a portion of the beam is reflected back towards the angle detection transducer 100. This may be achieved via diffusive reflection of the incident ultrasonic angle sensing beam.

Figure 8C:
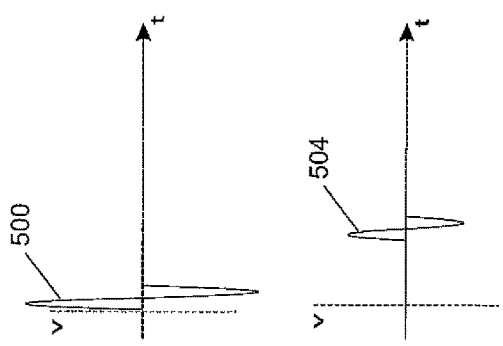
Figure 8D:
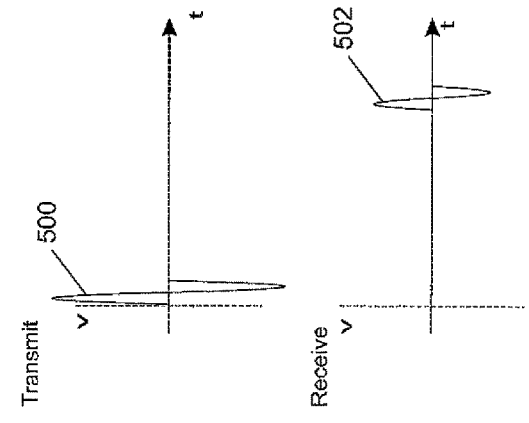
Figure 8E:
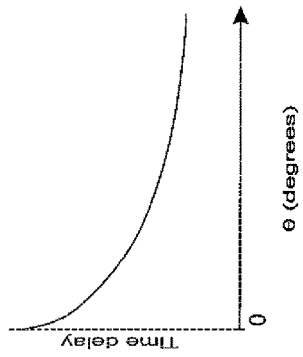
Figure 9E:
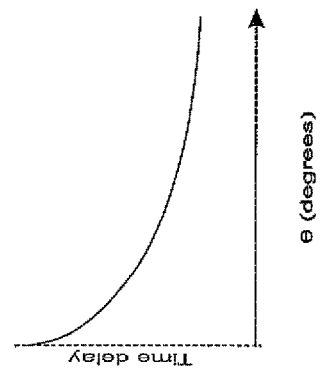
FIGS. 9a-9e demonstrate the use of a high frequency ultrasound transducer to estimate the angular orientation of an ultrasound transducer mounted on a deformable member.
Figure 9B:
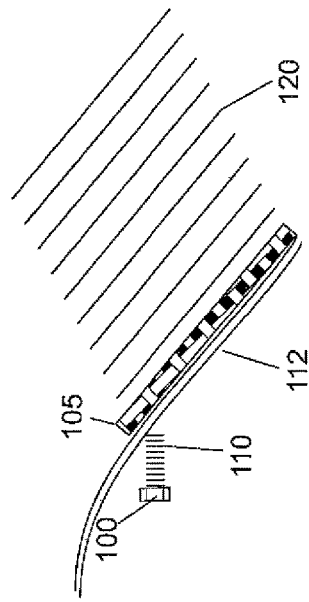
Figure 9A:
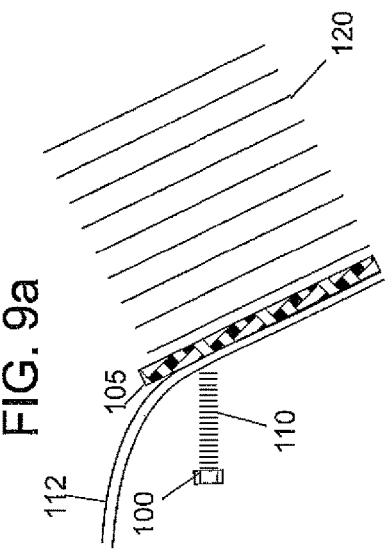
Figure 9D:
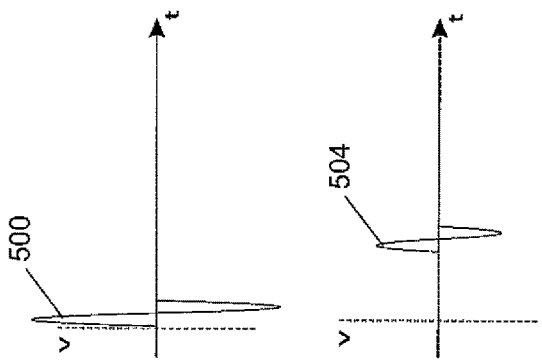
Figure 9C:
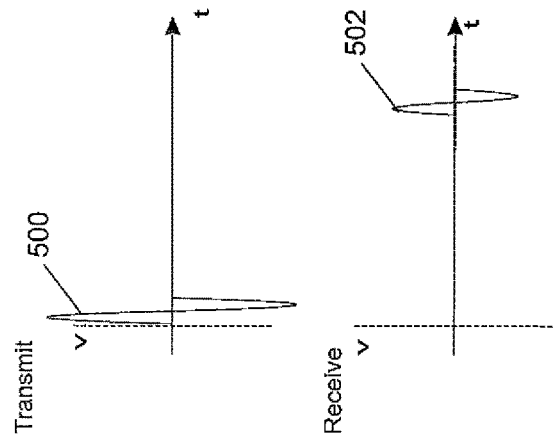

In FIG. 8a, tiltable member 150 is relatively far from the angle detection transducer 100, along the path of beam 110, when compared to FIG. 8b. This results in the angle detection beam 110 having a shorter time of flight in FIG. 8b than FIG. 8a. The tilt angle can be calculated as described above in reference to FIGS. 4a-e. Timing diagrams are presented for each angle scenario. A pulse is transmitted at t=0 with a high amplitude and received at a later time, typically with a reduced magnitude. FIG. 8e shows a sample plot of time delay, or time of flight vs. imaging angle. FIGS. 8c and 8d are timing diagrams are presented for each angle scenario in FIGS. 8a and 8b, respectively. The received pulse 502 corresponding to the signal from FIG. 8a has a much greater time delay that the received pulse 504 corresponding to the signal from FIG. 8b.

FIGS. 9a-9e illustrate an embodiment in which the change in angle of a tiltable member, such as ultrasonic imaging transducer 105 is detected using a time of flight method. This embodiment is similar to that of FIG. 7, except that ultrasonic imaging transducer 105 is not mounted on a pivoting axis, and is instead mounted on a deformable member 112 whose deformation is responsible for the tilting of the tiltable member.

FIGS. 10a-10e illustrates an embodiment in which the change of angle of tiltable member 101 (shown as an imaging transducer) is detected using a signal intensity method. This method is based on the relationship between the intensity of diffusively scattered ultrasonic radiation and the tilt angle, where the reflected signal will be strongest when the angle detection beam 110 is perfectly normal to tiltable member 101, as shown in FIG. 10a. As the tilt angle changes from normal, the strength of the received signal is reduced (item 504 vs. item 502), as is seen in FIGS. 10c and 10d. The reduction in received signal intensity or voltage can be used to estimate the tilt angle, as shown in the example calibration curve provided in FIG. 10e.

FIGS. 10c and 10d are timing diagrams presented for each angle scenario in FIGS. 10a and 10b, respectively. It is noted that there may be temporal broadening of the signal due reflections coming from different slightly different depths as the imaging transducer 101 is moved away from being normal to the angle detection beam 110. Such an effect is shown in FIG. 10d. Accordingly, in selected embodiments, the relative temporal broadening may also be employed to provide feedback relating to the deflection angle. Such an embodiment may be used to confirm and/or improve the accuracy of the deflection angle obtained through intensity measurements.

In some embodiments, the sensitivity of angle detection may be hindered at large deflection angles due to intensity reduction, as illustrated in FIGS. 10a-e. The intensity of a received signal from a perfect reflector drops very quickly from angles even slightly off normal from the angle detection beam 110. This makes the signals very difficult to detect, and diffusive reflectors may provide improved performance. There are several potential approaches to overcoming this.

The difference between a specular and diffusive reflector is illustrated in FIGS. 11a-d. FIG. 11a shows a specular reflective tiltable member 170 receiving an angle detection beam 110 from an angle detection transducer 100. The beam is reflected off the specular reflector 170, and the reflected beam 113 is directed in a path that is not co-incident with the angle detection transducer. The result, as shown in the timing diagram below in FIG. 11c, is that the pulse is not received.

FIG. 11b illustrates an embodiment in which the incident beam 110 is reflected by a diffusive reflector. While a portion of the beam 117 may be directed away in a similar fashion as described in FIG. 11a, a significant portion of the beam 115 is scattered and diffusively reflected over a wide angular range. A portion of this beam is collinear with the incident beam 110, thus allowing for a time of flight detection technique to be feasible (as shown in FIG. 11d by the presence of the reflected pulse).

Another potential arrangement that can assist with the reduction of signal from a substantially specular reflector is the use of multiple angle detection transducers. Such an embodiment is illustrated in FIGS. 12a-12d. Here, two angle detection transducers 100, 126 are oriented towards tiltable member 101 which is mounted on pivot axis 102. Each of the angle detection transducers 100, 126 generate their own acoustic beam 110, 127.

All 3 transducers of the preceding embodiment may be driven by a single electrical channel (for example, connected to patient interface module 36 of FIG. 1). Notably, there will be an overlap in the received signals from the angle detection transducers 100, 126 if they lie within the same frequency range. This can be resolved with prior knowledge of the transducer positions, or by limiting the range of angles through which the tiltable member is allowed to tilt.

Figure 12A:
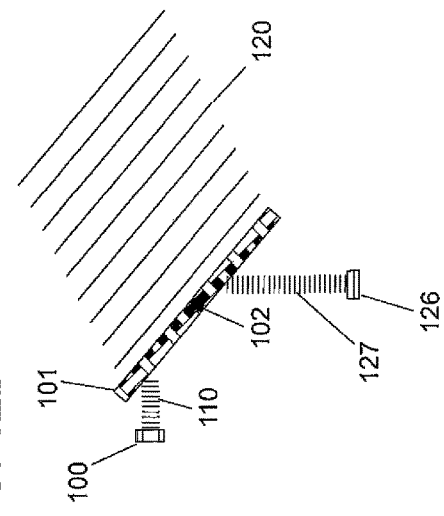
FIGS. 12a-d demonstrate the use of two high frequency ultrasound transducers to estimate the deflection angle of a tiltable component using a time of flight method, shown in (a) and (b) at two different angular orientations.
Figure 12B:
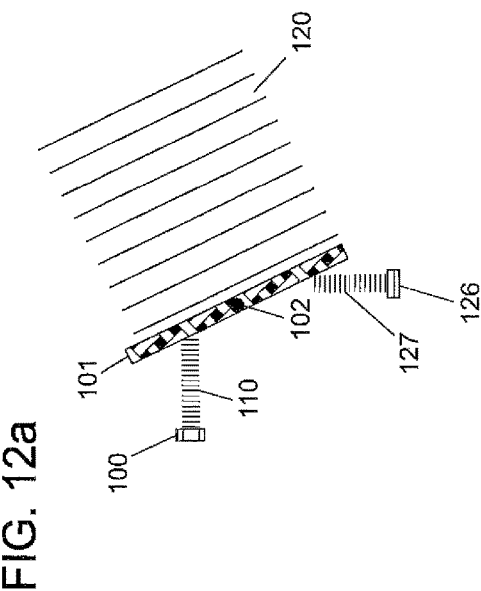
Figure 12C:
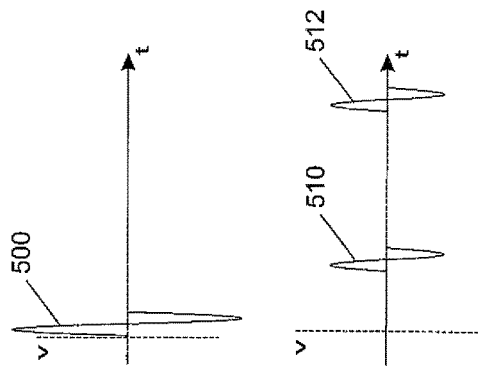
Figure 12D:
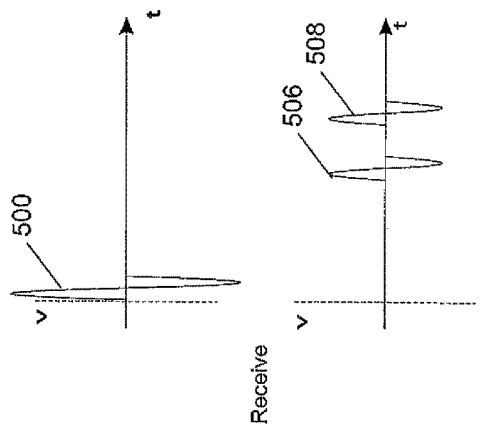
Figure 14A:
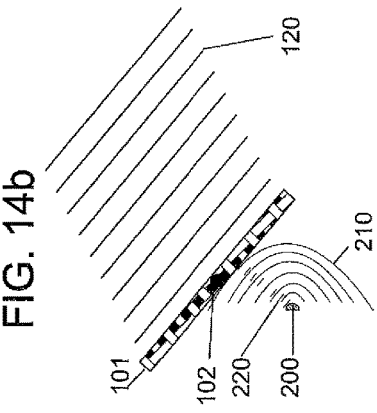
FIGS. 14a-d show the use of an ultrasound transducer that diffusely emits and detects ultrasound energy to increase the range of angles that can be detected using a time of flight method, shown in (a) and (b) at two different angular orientations.
Figure 14B:
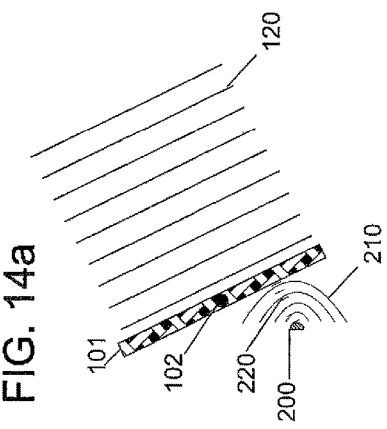
Figure 14C:
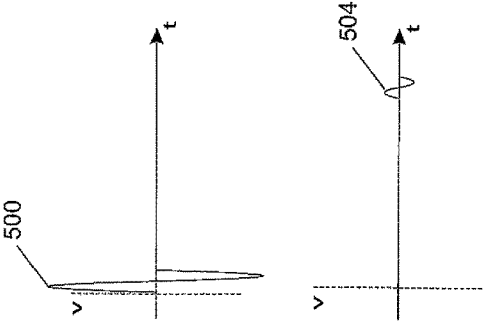
Figure 14D:
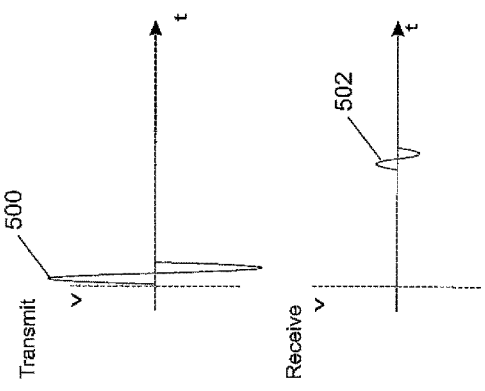

The distance calculated by the time of flight difference between the two received pulses may provide tilt angle information in this case. For instance, if the two angle detection transducers 100, 126 are placed 90° from each other with one of the beams parallel to the longitudinal axis, equidistant from pivot axis 102 and on opposing sides of pivot axis 102 but the same side of tiltable member 101 with a flat surface (as they are in FIGS. 12a-d), the difference in the time between the received pulses from both transducers will be at a minimum when the tilt angle is 45° from the longitudinal axis (As suggested by FIGS. 12c and 12d). As the tilt angle moves away from 45°, the time between the received signals between the two transducers will increase, as shown in FIG. 12d with received pulses 510, 512 from angle detection transducers 100, 126 respectively.

Angle sensing transducers 100 and 126 may be selected to have substantially non-overlapping spectral bandwidths, thus allowing the individual detected signals to be separated based on their frequency domain content. Alternatively, one of the angle sensing transducers may be placed further away from tiltable member 101 than the other, thus ensuring that the time delays from each of the angle sensing transducers is distinct from the time delay detected by the other angle sensing transducer.

Alternatively, knowledge of the expected direction and/or degree of tilt of the tiltable member can be used to algorithmically determine which portions of the sensed signal along the single electrical channel correspond to each of the two or more angle sensing transducers. For example, in the example implementation of an imaging probe having a movable member with an angular orientation that is dependent on the rotational speed of a rotational conduit housed within the imaging probe, if the rotational speed of imaging assembly 50 along the longitudinal axis of imaging probe 44 is increased, it may be expected that the tiltable member would tilt in a more forward looking direction. Therefore, knowledge of the expected direction of tilt could be used to identify which of the peaks in the received signal corresponds to one of the several angle sensing transducers. Similarly, knowledge of the instantaneous rotational velocity of the imaging assembly may correspond with a greater likelihood to a particular range of tilt angles, and such a relationship could be used to identify which of the peaks of the received signal most likely corresponds to one of the several angle sensing transducers.

FIGS. 13a-13e illustrates an embodiment that enables sensitive angular detection while increasing the range of angles that can be detected by the angle detection transducer 100. In this embodiment, the back surface of tiltable member 183 (which may also include an imaging transducer, as shown in FIGS. 13a-e) has been shaped with a series of curved indentations. As the transmitted beam 110 hits the back of tiltable member 183, a small portion of the reflective interface will be substantially normal to the incident beam 110, causing part of the beam 181 to be reflected back to angle detection transducer 100. Accordingly, the angle can be resolved using a time of flight method similar to FIGS. 4a-e. It is to be understood that the specific cylindrical surface patterning illustrated in FIGS. 13a-e is merely one non-limiting embodiment, and that a wide range of surface profiles may be employed to achieve a similar result according to the present embodiment. For example, parabolic cross-sections, or a pattern of divots may be used on the back surface of tiltable member 183.

While the preceding embodiments have disclosed surfaces that are diffusively reflective, it is to be understood that diffusive reflections may be generated by surface and/or volume material properties. For example, particles of metals, ceramics, silicon dioxide, graphite, glass beads, or other compounds known in the art can be added to a material or surface to make it more diffusely reflective.

The use of composite materials or flexible polymers has allowed for ultrasound imaging transducers to be shaped physically. Such transducers may be employed for focusing acoustic energy. Alternatively, acoustic lenses may also be used to focus acoustic energy. However, such schemes may be adapted to the present embodiments to broaden the acoustic beam and support an increase in the range of angles that can be detected. This is illustrated in FIGS. 14a-14d, where angle detection transducer 200 is curved such that it creates diverging beam 210. As shown in the Figure, a portion of the beam is normal to the imaging transducer 101 at a wide range of angles. The normal portion of the beam 220 is reflected back to the transducer, even when the tiltable member is a specular reflector, and may be measured to estimate tilt angle using a time of flight method as in FIGS. 4a-e.

Yet another embodiment for increasing the range of angles that can be detected may be achieved by attaching the angle detection transducer to the tiltable member. FIGS. 15a-15e shows an example of one such embodiment. In this embodiment, angle detection transducer 100 is mounted to the back of the tiltable member 101. The angle detection beam 110 is directed towards stationary reflector 174. A portion of stationary reflector 174 may be curved (in any of several shapes) to provide a suitable angle-dependent acoustic reflection profile. Example yet non-limiting curvature profiles include circular, elliptical or parabolic shapes.

Figure 15A:
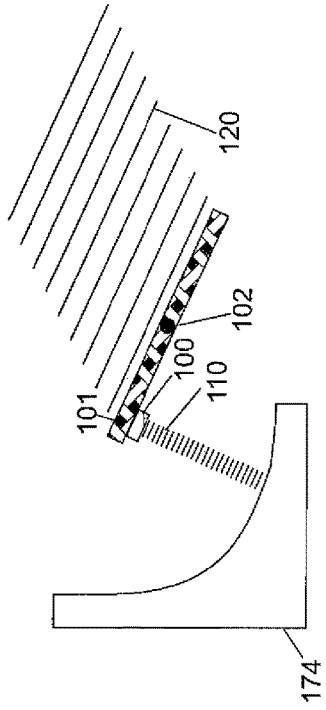
FIGS. 15a-d show the use of a curved surface to increase the range of angles that can be detected with improved precision using a time of flight method with an angle detection transducer attached to a tiltable component, shown in (a) and (b) at two different angular orientations.
Figure 15B:
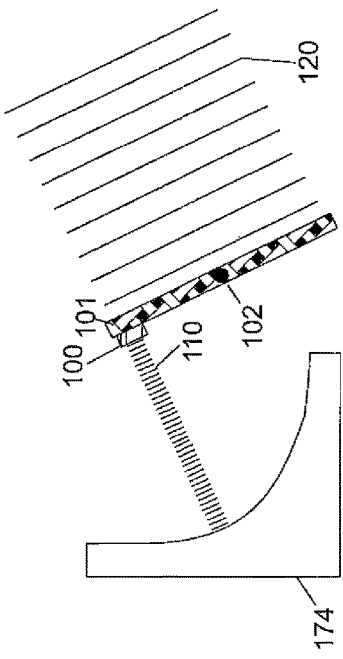
Figure 15C:
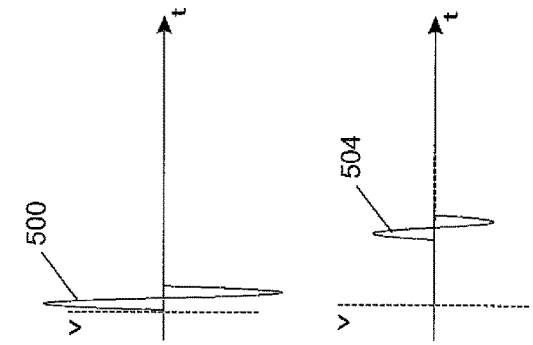
Figure 15D:
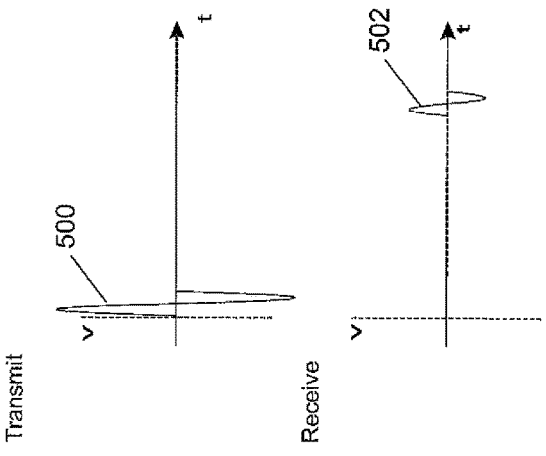

In one embodiment, the stationary reflector 174 may be shaped so that over a wide range of imaging transducer 101 tilt angles, the reflection from the angle detection beam 110 is largely retro-reflected towards the angle detection transducer 100. As shown in FIGS. 15c and 15d, one or both of the time of flight and intensity schemes may be employed to infer changes in the orientation of tiltable member 101.

Figure 15E:
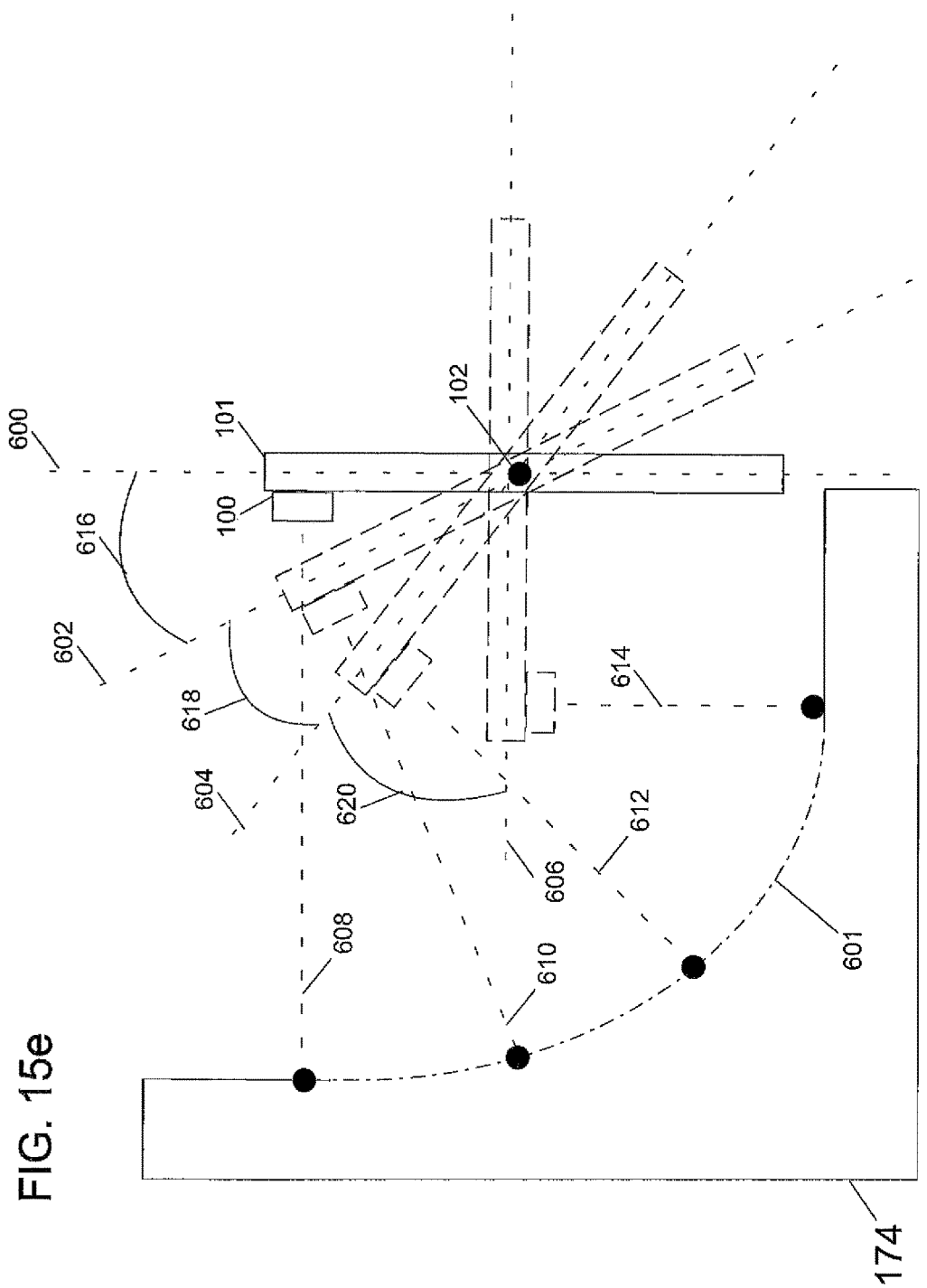
FIG. 15e illustrates the relationship between the curvature of the surface and the orientation of the transducer, such that the surface is locally approximately normal to the incident acoustic beam to ensure strong received signals.

FIG. 15e describes one method to design a stationary retroreflecting acoustic reflector. The angle detection transducer 100 is modeled in a forward viewing position, as defined by tilt axis 600. A desired distance 608 between angle detection transducer 100 and the reflecting surface is chosen and a data point is generated on a line normal to transducer 100 a distance 608 away from transducer 100. The angle detection transducer is tilted by angle 616 about pivot point 102 and desired distance 610 between angle detection transducer and reflecting is chosen to differ from 608 by a selected amount, such as an amount for obtaining a desired angular resolution. A data point is generated as with the above. This process is repeated until the angle detection transducer is tilted to the point that it is side viewing. A continuous surface 601 is defined by interpolating the data points generated as described above using known curve fitting techniques. Examples of suitable curves that can be fitted are portions of an ellipse, parabola, circle, hyperbola, exponential, roulette, or polynomial using fitting strategies common in the art including but not limited to ordinary least squares or total least squares.

Once a surface is defined and fabricated, there may be imperfections in machining tolerances and misalignments in assembly among other uncertainties. In order to mitigate this, calibration of an angle detection assembly may be used to overcome these imperfections.

According to another embodiment, the surface 601 is defined such that the angle detection beam emitted by the angle sensing ultrasonic transducer 100 is substantially retroreflected over a given range of pivot angles, such that the distance between surface 601 and angle sensing ultrasonic transducer 100 varies monotonically over the range of pivot angles, and such that the rate of change of the relative distance with respect to the pivot angle (which, at least in part, determines the resolution of the apparatus), exceeds a minimum value over the range of pivot angles. In one embodiment, surface 601 is configured such that the rate of change of the relative distance with respect to the pivot angle is substantially constant over the range of pivot angles, such that the sensitivity of the apparatus is substantially independent of pivot angle over the range of pivot angles.

As noted above, in some embodiments, the angle of the detection beam may be constrained to remain approximately normal to the reflective surface of the tiltable member, thereby generating a retroreflection. This eliminates the need to compensate for reflections at angles where the angle detection beam is not normal to the tiltable member, and generally results in detected beam of higher intensity. Example embodiments utilizing such an approach are shown in FIGS. 16 and 17. FIGS. 16 a-d illustrate an embodiment in which angle detection transducer 100 is mounted onto second tiltable member 114 that is mechanically linked or coupled to first tiltable member 101 via coupling mechanism 176. Secondary tiltable member 114 is not necessarily acoustically active (and may be acoustically passive) and allowed to pivot about axis 104.

Since both members are able to pivot about their own pivot axes and are mechanically coupled, they will tilt in unison. The tiltable members are mechanically coupled such that they tilt with a substantially equal tilt angle during operation. A number of techniques may also be used to couple the motion of the tiltable members, including, but not limited to, rods, beams, magnets, and electromagnetic devices. The embodiments shown in FIGS. 16 and 17 have the additional benefit of adding another tiltable member to the system that may not suffer from inertial or other design constrains of the first tiltable member, such as being an ultrasound transducer optimized for acoustic performance.

Figure 4G:
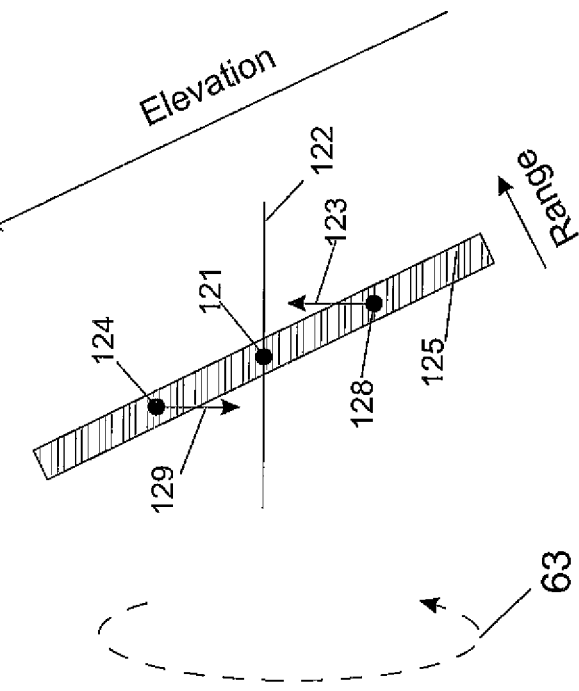
FIG. 4g shows a body where the dimension in the range direction is much smaller than the dimension in the elevation direction.
Figure 4F:
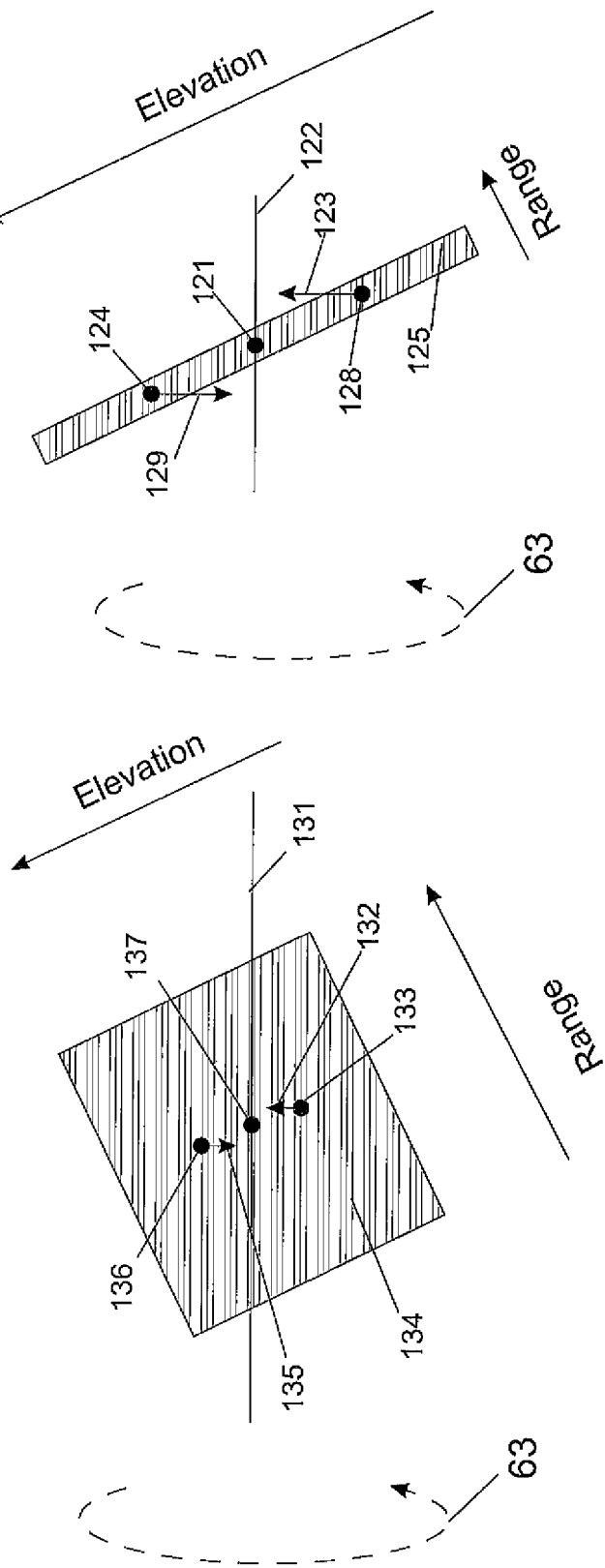

Such a scheme may be useful in cases where first tiltable member includes an ultrasonic imaging transducer, but does not possess suitable characteristics for external rotational actuation. By incorporating secondary tiltable member 114 with characteristics designed for actuation via external rotation and mechanically linking both tiltable members, first tiltable member 101 can be actuated based the behavior of second tiltable member 114. For example, as shown in FIGS. 4f and 4g, ultrasound transducers may have similar or larger dimensions in the range direction compared to the elevation directions. This is largely due to the requirement for backing on an ultrasound transducer to attenuate signals in directions other than the desired imaging direction. Bodies of this geometric configuration are not ideal for actuation via external rotation, as shown in FIGS. 4f and 4g.

FIG. 4f shows a body 134 that has a similar dimension in the range direction relative to the elevation direction. Here, the body pivots about point 137 under rotation in direction 63. If the body is broken into two components, one above longitudinal axis 131 and one below, the center of mass of the components above and below longitudinal axis 131 are shown at 136 and 133 respectively. The centripetal force vectors are shown as 135 and 132 respectively.

Now, comparing to a body shown in FIG. 4g, where the dimension in the range direction is much smaller than the dimension in the elevation direction, we see similarly that the body pivots about point 121 under rotation in direction 63. If the body is broken into two components, one above longitudinal axis 122 and one below, the center of mass of the components above and below longitudinal axis 122 are shown at 124 and 128 respectively. The centripetal force vectors are shown as 129 and 123 respectively. The result is that the pivotally mounted body 125 in FIG. 4g has a much stronger relative component of centripetal force that acts to cause tilt about the pivot point 121 than body 134 does about pivot point 137.

This mechanical coupling may also allow angle detection beam 110 to remain normal to the ultrasound imaging transducer 101. Other techniques that additional deflectable member can employ to assist in deflection may include the use of hydrofoil features or artificial muscle actuation.

A time of flight technique can be used to estimate the imaging angle, similar to that shown in FIGS. 4a-e. Alternatively, or additionally, an intensity measurement method may be employed, as illustrated in FIGS. 10c and 10d.

Figure 16A:
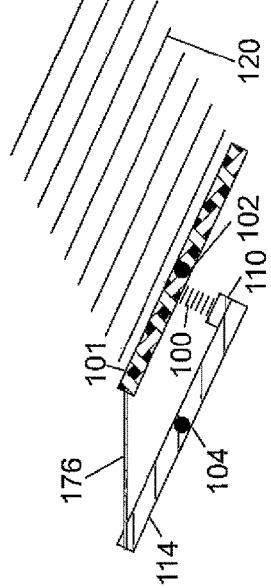
FIGS. 16a-d show the use of a high frequency ultrasound transducer to estimate the tilt angle of a tiltable ultrasound transducer mechanically coupled to an otherwise acoustically passive component with the angle detection transducer mounted on the otherwise acoustically passive component, shown in FIGS. 16a and 16b at two different angular orientations.
Figure 16B:
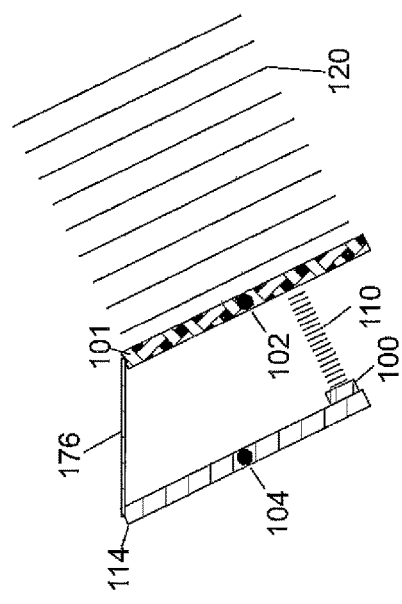
Figure 16C:
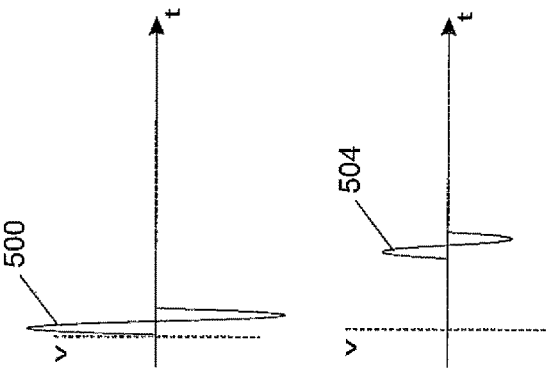
Figure 16D:
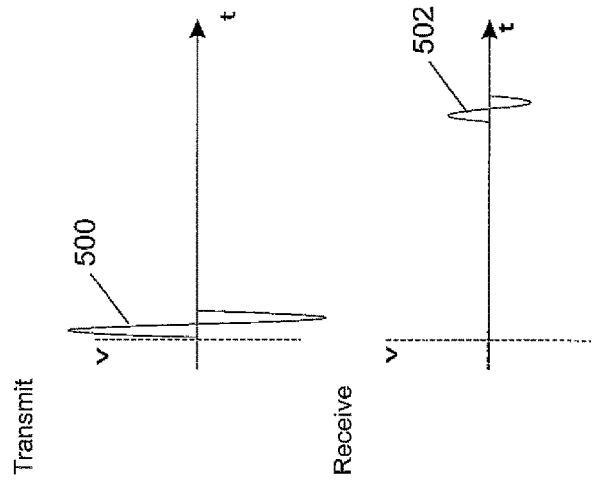
Figure 16E:
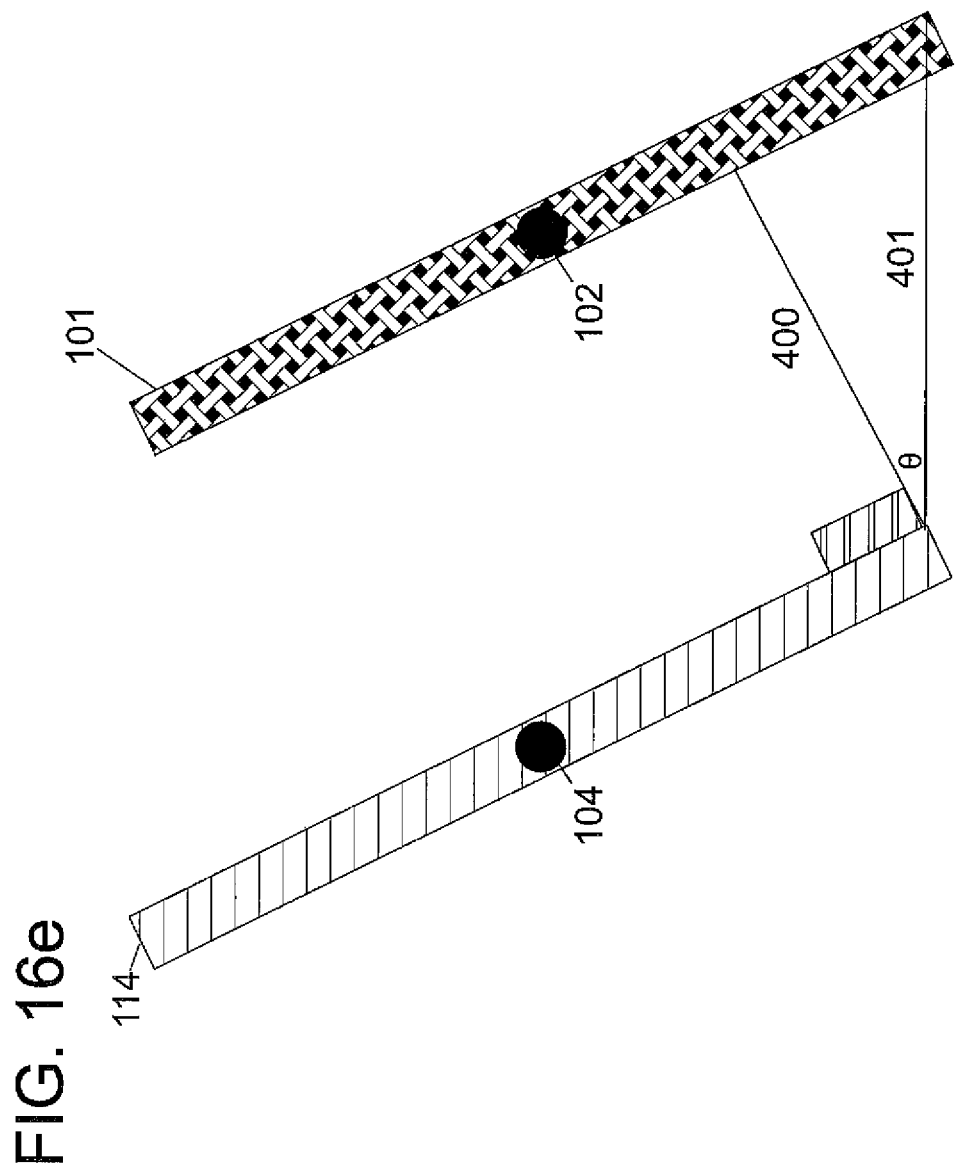
FIG. 16e shows some geometric relationships that can be used to calculate the tilt angle from the knowledge of the distance between angle detection transducer and a constant distance between a point on each of two tiltable components.
Figure 17A:
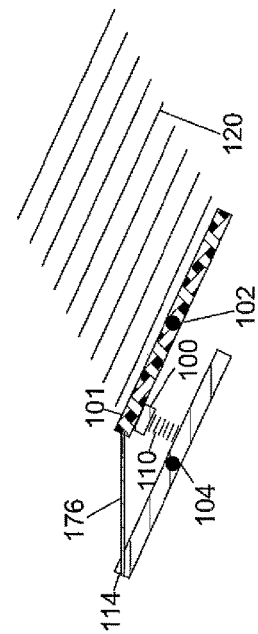
FIGS. 17a-d show the use of a high frequency ultrasound transducer to estimate the deflection angle of a tiltable ultrasound transducer mechanically coupled to an acoustically passive component with an angle detection transducer integrated onto an imaging transducer.
Figure 17B:
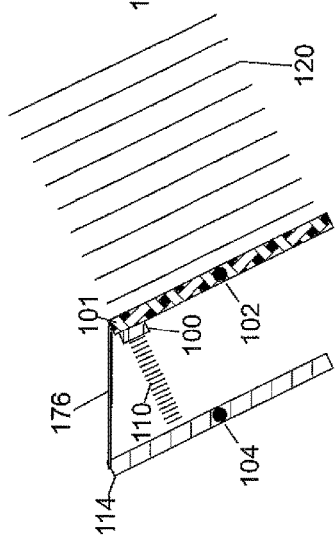
Figure 17C:
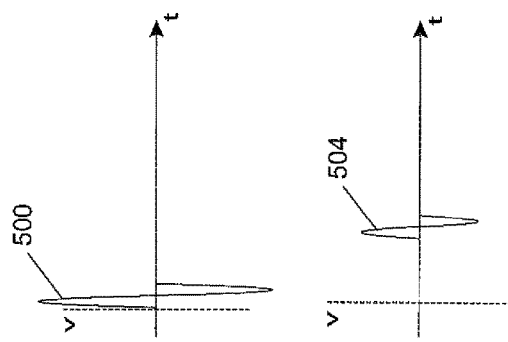
Figure 17D:
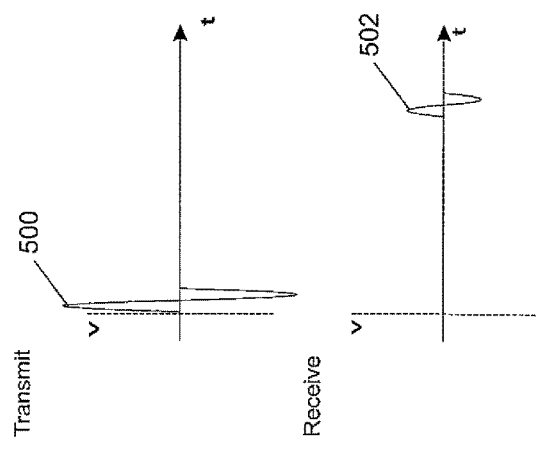

FIG. 16e illustrates some of the parameters that may be employed to calculate the tilt angle θ based on measured distance 400. If the distance 401 between acoustically passive disc 114 and the imaging transducer 101 is constant and known a priori, and the distance between the angle detection transducer 100 and the imaging transducer 101 is determined with the knowledge of the signal time of flight and the speed of sound in the medium, the angle can be calculated with the trigonometric equation θ=arcCos(measured_distance 400/known_distance 401).

In a similar embodiment, illustrated in FIGS. 17a-17d, angle detection transducer 100 can be mounted on the tiltable member 101, and maintained in a normal orientation relative to acoustically passive tiltable member 114. A unitary structure similar to that shown in FIG. 5a would be suitable for use as the tiltable member 101 in FIG. 17a.

FIG. 18a illustrates an embodiment that combines the features shown in FIGS. 15 and 17. Here, the stationary curved reflector 174 is employed to increase the range of angles that can be detected using the angle detection transducer 100. This is achieved by separating the imaging transducer 101 and the acoustically passive tiltable member 114 in space sufficiently such that they do not come into contact with each other regardless of tilt angle (within the range permitted during operation), while still allowing the acoustically passive second tiltable member 114 to be employed to assist the ultrasound imaging transducer 101 in achieving desired motion using mechanical coupler 176.

FIG. 18b shows a view cut of an example embodiment through the hatched line in FIG. 18a. A notch 177 in the stationary curved reflector 174 is created such that the mechanical coupler 176 is allowed to pass through the stationary reflector 174 unimpeded. By way of example, mechanical coupler 176 may include a simple bar or rod that is connected to each of the tiltable members 114 and 101 by a hinge or other mechanism, such as a mechanism that creates a pivot point or deformable joint between mechanical coupler 176 and each of the tiltable members.

Figure 18D:
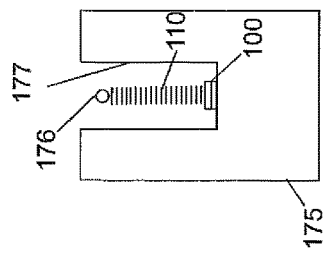
FIGS. 18c-18i show an embodiment in which the position of the mechanical coupler is detected using the angle detection transducer to estimate the angle of deflection.
Figure 18F:
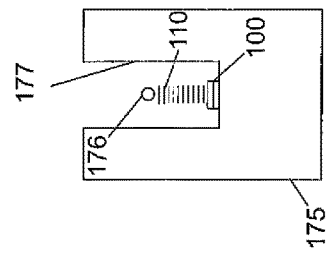
Figure 18I:
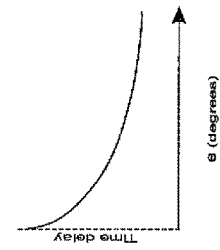
Figure 18C:
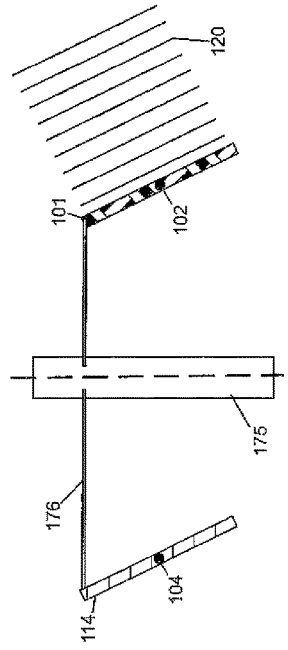
Figure 18E:
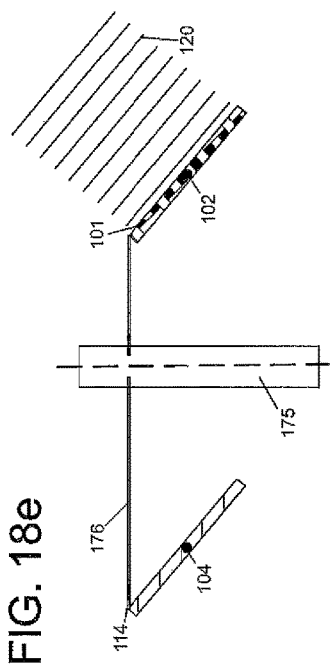
Figures 18G, 18H:
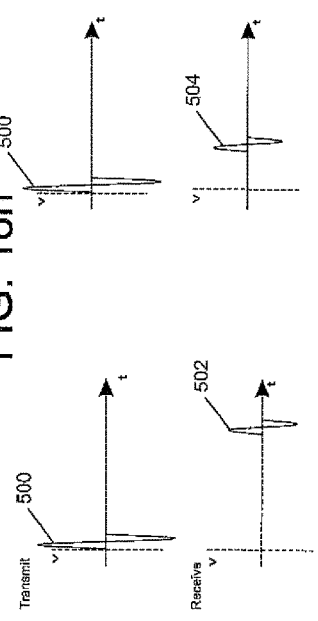

FIGS. 18c-i demonstrate another apparatus for detecting tilt angle where the angle detection transducer 100 is mounted inside the notch 177 of supporting structure 175 instead of being attached to the tiltable member 101. FIGS. 18c and 18e show the setup at two different tilt angles. Cut view through the hatched lines in FIGS. 18c and 18e are shown in FIGS. 18d and 18f respectively. FIGS. 18g and 18h show the timing diagrams for FIGS. 18d and 18f respectively. In FIG. 18d, the mechanical coupling bar 176 is near the top of the notch 177 resulting in the received signal in 18g having a long delay, whereas in FIG. 18f it is considerably further down within the notch, and is subsequently closer to the angle detection transducer resulting in a received signal with a shorter time delay. FIG. 18i shows a plot estimating deflection angle vs. time delay. Alternatively, the angle detection transducer 100 can be mounted on mechanical coupling bar 176 and pointed towards the bottom of notch 177.

FIGS. 18c-i show how a second transducer 100 can be used to detect the position of a component within an imaging probe. While the position information may be used to infer the tilt angle of a tiltable component, the ability to more generally gather information about the position of a movable component within an imaging probe by using a second transducer that shares a common single channel with another ultrasound transducer becomes apparent.

Although FIG. 18 provides one example embodiment in which an additional ultrasonic transducer is employed for detecting changes in a position of a movable component, it is to be understood that this embodiment may be employed in a wide number of applications for detecting motion of a component within an ultrasonic probe. Other illustrative examples in which the motion of a component may be detected include features in the sheath during a pullback operation, a retractable sheath, the presence of bubbles, a change in fluid density in the catheter, or a therapeutic tool such as a Brockenborough needle.

Accordingly, it is to be understood that the scope of the embodiments disclosed herein is not to be limited to those in which an angular orientation or a change in an angular orientation of a movable component is determined using one or more additional ultrasonic transducers, and further encompasses embodiments in which a position or a change in position of a movable component is determined using one or more additional ultrasonic transducers, irrespective of whether or not the position or change in position relates to an angular orientation or a change in angular orientation.

FIG. 19 shows an example time-domain imaging and angular detection sequence for a single pulse-echo ultrasound imaging sequence using the embodiment described in FIGS. 17a-d. In FIG. 19a, imaging transducer 101 is excited with a low frequency pulse, as shown in the timing diagram shown in FIG. 19b. The pulse generates an acoustic beam 120 which propagates until it reaches an object 106 in its path.

Part of the beam is reflected, and detected by the imaging transducer, and as a result displayed in the "Receive" portion of the timing diagram. Next, the residual beam meets another object 108, and again, a part of the beam is reflected, and detected by the imaging transducer and likewise appears as a received signal, slightly further along the "Receive" timing diagram.

After imaging data is received, a high frequency angle detection pulse is transmitted down the same channel, generating an acoustic beam 110 from the angle detection transducer 100. This beam is reflected off the acoustically passive member 114 and returned to the transducer. The tilt angle is determined using the time of flight of the beam 110 following the high frequency pulse generation.

As described above, this embodiment can be optionally aided with the use of one or more electronic filters to select the desired frequency components. For example, a low pass filter may be used to emphasize low frequency signals from the low frequency imaging transducer 101 following transmission of an imaging pulse 550, while a high pass filter may be used to emphasize the high frequency signals from high frequency angle detection transducer 100 following the transmission of angle detection pulse 500. These filters may reside within the imaging probe, or optionally external to the imaging probe, such as within controller and processing unit 34 or patient interface module 36.

Figure 19C:
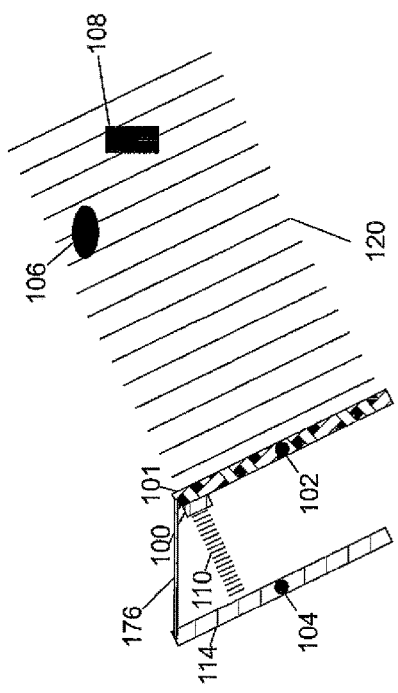
Figure 19D:
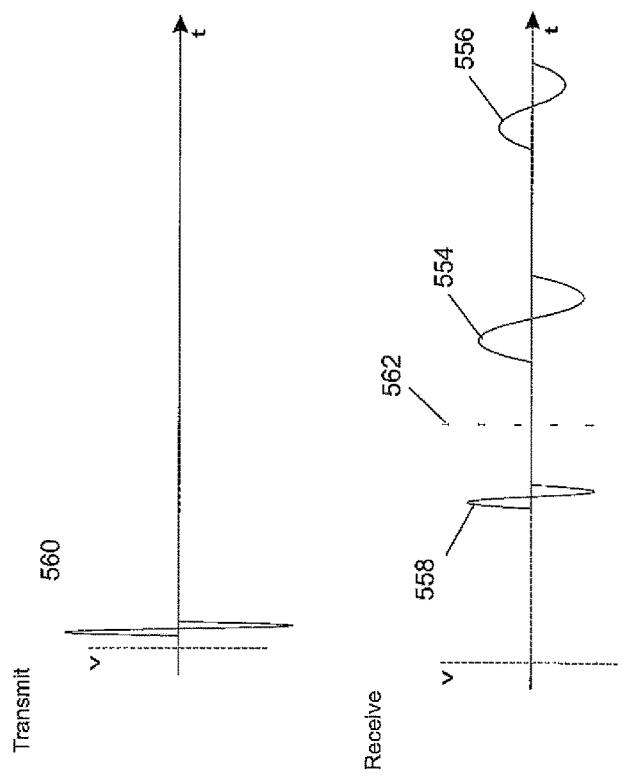
Figure 19E:
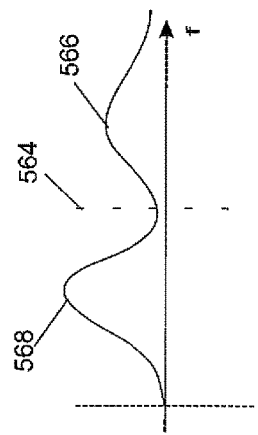

FIG. 19c-e shows an embodiment where both transducers are excited with a broadband pulse that covers the bandwidths of both imaging transducer 101 and angle detection transducer 100. The received signal from both transducers is demultiplexed in order to separately process the imaging signal data and the angle sensing data. Such demultiplexing may be achieved according to one of many embodiments.

In one such discriminatory embodiment, as described in FIG. 19d, a time domain method is employed utilizing the fact that there may be a significant difference in the distance between a) the angle detection transducer 100 and the second deflectable member 114 and b) the imaging transducer 101 and the acoustic imaging targets 106 and 108. The distance between the angle detection transducer 100 and the second deflectable member 114 may be significantly less than the distance between the imaging transducer 101 and the acoustic imaging targets 106 and 108. In this arrangement, signals received 558 shortly after transmission 560 pulse is sent may be deemed to be as a result of the angle detecting transducer 100, and signals received after later time delays 554, 556 may be deemed to be as a result of the imaging transducer 101. Accordingly, in such an embodiment, all pulses received prior to the vertical hatched line 562 are deemed to be angle detection pulses and those received after are deemed to be imaging pulses.

A second embodiment for demultiplexing the signals may be achieved by spectrally filtering or separating the spectral content contained within the net signal and can be achieved using the same embodiment shown in FIG. 19c. A representative timing diagram is shown in FIG. 19d as described above. Since the bandwidths of the transducers are sufficiently separated and may be known, signals falling within the bandwidth of the angle detection transducer 100 can be deemed to be originating from the angle detection transducer 100, and signals falling within the bandwidth of the imaging transducer can be deemed to be originating from the imaging transducer.

This spectral separation is shown the spectral plot in FIG. 19e, where the vertical hatched line 564 is used to show a point representing the separation between imaging data and angle detection data. This line may be the midpoint between the center frequencies of the two transducers. All spectral components lower than the frequency represented by the hatched line are deemed to be components of the imaging signal 568, and all spectral components higher than the frequency represented by the hatched line are deemed to be components of the angle detection signal. Also, the separation may be defined more than a single line. For instance, the −6 dB, −20 dB or −40 dB bandwidths may be used as points to separate data between angle detection and imaging. Furthermore, the both the time of flight demultiplexing and spectral demultiplexing techniques described for FIG. 19c-e above can be combined.

It is to be understood that there are many methods that can be employed to obtain sufficient spectral isolation of the two signals. As described above, filtering techniques may be employed to separate the spectral signals received from each transducer. In another embodiment, spectral windows corresponding to each transducer may be determined based on an isolation criteria. For example, the upper end of the spectral window for the lower-frequency transducer may be selected as corresponding to the point at which the spectral response of the higher-frequency transducer falls below a desired value (for example, 20 dB).

In some situations, it may be desirable to excite the ultrasound transducers at different points in time, with differing repetition frequencies. One example of this is where one of the transducers is configured for angle detection. In this scenario, changes in angle may be extremely minute such that it may be unnecessary to perform angle detection with at the pulse repetition rate required for imaging. For example, it may be that the angle is expected to remain relatively constant over the amount of time required to acquire multiple imaging vectors. A pulse sequence can be defined such that imaging pulses 550 are transmitted and acquired much more frequently than angle detection pulses 500, as shown in FIG. 19f.

Similarly, it may be desirable in some situations to allow more time for echo return from one ultrasound transducer than the other. One example of this is where one of the transducers is configured for angle detection. In this scenario, it is often the case that the transducer configured for angle detection is of higher frequency that the transducer configured for imaging. Furthermore, it is often the case that the angle detection is performed using echoes from locations that are spatially very close to the angle detection transducer, requiring relatively little acquisition time to ensure capture of echoes associated with angle detection.

This scenario is illustrated in FIG. 19g. Imaging pulse 550 is transmitted and a relatively long period of time 420 is dedicated to waiting for echoes associated with imaging pulse 550. Conversely, relatively little time 422 is dedicated to waiting for echoes associated with angle detection pulse 500.

In some embodiments, the temporal spacing between imaging pulses may be configured to be variable. By way of example, in situations where a motor encoder is used as a trigger for imaging pulses, the imaging pulse repetition frequency will be higher the motor is rotating more quickly than when the motor is rotating more slowly. Accordingly, the pulse repetition frequency for angle detection may also be selected to be variable, and to be determined by the pulse repetition frequency of imaging.

It is to be understood that FIGS. 4, and 8 through 19 represent embodiments that are typically housed within the imaging assembly 50, but that the other components of the imaging assembly are not shown for simplicity.

FIG. 20 illustrates three different techniques for calculating the relative distance travelled by the ultrasonic angle sensing beam, based on the detected radio-frequency (RF) signals. The first method, shown in FIG. 20a, involves calculating the peak value of the RF signal for each pulse. As shown, the received electronic pulse includes a pulse envelope and oscillations of a carrier wave. The first pulse 402 is shown as arriving relatively early compared to the second pulse 404. This implies that the angle detection transducer 100 is closer to the tiltable member 101, with the first pulse 402 (for example, as shown in FIG. 4b) than the second pulse 404 (for example, as shown in FIG. 4a). The difference 414 between the peak RF value 406 from the first signal and the second signal 408 can be used to estimate the distance between the two points which can then be used to infer the tilt angle.

However, the RF signal in the carrier wave can fluctuate significantly as a result of minor changes in sub-resolution scatterers, and it follows that using the RF peak detection method can lead to inaccuracies when measuring small changes in position. For example, if a new peak emerges, there will be significant error in the measurement of distance between the angle detection transducer and the imaging transducer.

Another approach is to first calculate the envelopes of signals (407 and 409 for RF signals 402 and 404 respectively) and using the difference 416 between the envelope peaks (410 and 411 for envelopes 407 and 409 respectively) to estimate distance. Some of the fluctuation issues described with using the RF peak method are eliminated with this technique.

Another example employs the cross correlation between two signals to estimate the distance between subsequent received RF pulses. An example embodiment is shown in FIG. 20*b*. The cross correlation between the first 402 and second 404 RF pulses is shown as 413, with the peak of the cross correlation signal being detected as 412. The amount of time between time 0 and the peak value is given as 418 and can be used to calculate the distance travelled between two tilt angles to calculate angular shift.

Generally, the cross-correlation may be performed between a given pulse and another recorded pulse, such as a previously recorded pulse obtained at a different angular tilt. Alternatively, the cross correlation may be performed between a given pulse and a pulse stored at time of calibration of the imaging probe and retrieved from the EEPROM or other memory mechanism associated with imaging probe 44. Alternatively, the cross correlation may be performed between a given pulse and a standardized pulse for a particular design of imaging probe 44, assuming that the pulses generated by the angle detecting transducer are adequately reproducible between imaging probes fabricated from the same design.

Figure 21:
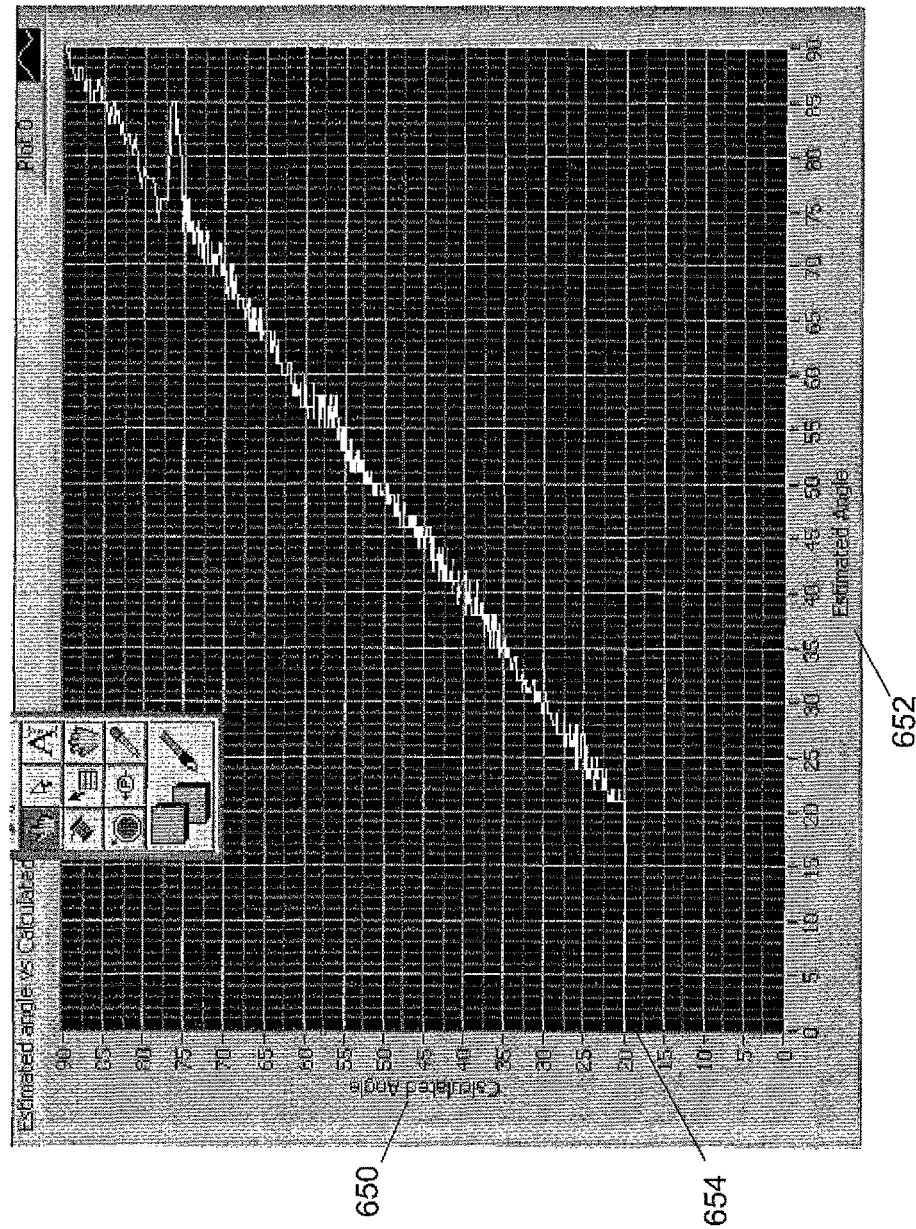
FIG. 21 shows experimental data obtained from an angle detection experiment conducted with the embodiment described in FIGS. 18a and 18b.

In the preceding angle-detection embodiments, outliers may be detected and rejected to improve the performance angle detection. There are several known techniques for rejecting outliers which could be applied including statistical techniques and voting methods. FIG. 21 shows experimental measurements of using an angle detection scheme corresponding to the embodiment described in FIG. 18*a*. Distances between two tiltable disc-shaped members were calculated using the cross-correlation method from FIG. 20*b*. The tiltable members were tilted using a microstage that continuously advanced a rod against the surface of one of the tiltable members causing the two tiltable members to tilt in unison. The position of the rod (in microns) is shown on the x-axis. The normal distance measured between the two tiltable members as measured by an angle detecting transducer on one of the tiltable members is shown on the y-axis (in microns), as depicted in FIGS. 17*a-d*. The tilt angle subtended by the tiltable members with an arbitrary axis could be calculated at each time point based on the measured distance between the two members. This angle was compared to the expected angle based on a solid model.

The specific embodiments described above have been shown by way of example, and it should be understood that these embodiments may be susceptible to various modifications and alternative forms. It should be further understood that the claims are not intended to be limited to the particular forms disclosed, but rather to cover all modifications, equivalents, and alternatives falling within the spirit and scope of this disclosure.

Therefore what is claimed is:

1. An ultrasound imaging probe comprising:
    a hollow sheath;
    an imaging conduit extending through said hollow sheath, said imaging conduit comprising electrically conductive paths that define an electrical channel;
    an imaging assembly supported remote from a proximal end of said imaging conduit, said imaging assembly comprising:
        a solid support;
        an ultrasound transducer in electrical communication with said electrically conductive paths;
        one or more pivot elements contacting said ultrasound transducer and pivotally supporting said ultrasound transducer relative to said solid support; and
        a spring connecting said ultrasound transducer to said solid support, such that said spring provides a restoring force in response to pivotal motion of said ultrasound transducer.

2. The ultrasound imaging probe according to claim 1 wherein said spring is a torsion spring pivotally connecting said ultrasound transducer to said solid support.

3. The ultrasound imaging probe according to claim 2 wherein said torsion spring is electrically conductive and forms an electrical connection between said ultrasound transducer and one of said electrically conductive paths.

4. The ultrasound imaging probe according to claim 2 wherein an axis of said torsion spring is collinear with a pivot axis of said ultrasound transducer.

5. The ultrasound imaging probe according to claim 2 wherein said torsion spring is a first torsion spring contacting a first side of said ultrasound transducer, said imaging assembly further comprising a second torsion spring pivotally connecting a second side of said ultrasound transducer to said solid support.

6. The ultrasound imaging probe according to claim 5 further wherein said first torsion spring and said second torsion spring respectively form electrical connections between said ultrasound transducer and said electrically conductive paths.

7. The ultrasound imaging probe according to claim 6 wherein said ultrasound transducer comprises a piezoelectric layer and a backing layer, and wherein a first lateral electrode and a second lateral electrode are located on respective lateral surfaces of said backing layer, wherein said first lateral electrode and said second lateral electrode are in electrical communication with respective actuation electrodes contacting said piezoelectric layer, and wherein said first lateral electrode and said second lateral electrode are respectively in electrical communication with said electrically conductive paths.

8. The ultrasound imaging probe according to claim 3 wherein an electrically conductive portion of said spring includes a material selected from the group consisting of stainless steel, beryllium copper, copper, silver, titanium, gold, platinum, palladium, rhenium, tungsten, nickel, cobalt, and alloys thereof.

9. The ultrasound imaging probe according to claim 3 wherein said spring includes an electrically conductive core and an electrically insulating coating.

10. The ultrasound imaging probe according to claim 2 wherein said torsion spring includes a wire having cross-sectional dimensions on a micron scale.

11. The ultrasound imaging probe according to claim 10 wherein said cross-sectional dimensions are between 2 microns and 100 microns.

12. The ultrasound imaging probe according to claim 1 wherein said spring is electrically conductive.

13. The ultrasound imaging probe according to claim 12 wherein said spring includes an electrically conductive core and an electrically insulating coating.

14. The ultrasound imaging probe according to claim 12 wherein an electrically conductive portion of said spring includes a material selected from the group consisting of stainless steel, beryllium copper, copper, silver, titanium, gold, platinum, palladium, rhenium, tungsten, nickel, cobalt, and alloys thereof.

15. A pivotable ultrasonic apparatus with restricted pivotal motion, comprising:

a solid support;

an ultrasound transducer;

one or more pivot elements contacting said ultrasound transducer and pivotally supporting said ultrasound transducer relative to said solid support; and a spring connecting said ultrasound transducer to said solid support, such that said spring provides a restoring force in response to pivotal motion of said ultrasound transducer.

16. The apparatus according to claim 15 wherein said spring is a torsion spring pivotally connecting said ultrasound transducer to said solid support.

17. The apparatus according to claim 16 wherein an axis of said torsion spring is substantially collinear with a pivot axis of said ultrasound transducer.

18. The apparatus according to claim 16 wherein said torsion spring is a first torsion spring contacting a first side of said ultrasound transducer, the apparatus further comprising a second torsion spring pivotally connecting a second side of said ultrasound transducer to said solid support.

19. The apparatus according to claim 18 further wherein said first torsion spring and said second torsion spring are electrically conductive and are configured for electrically addressing said ultrasound transducer.

20. The apparatus according to claim 16 wherein said torsion spring is electrically conductive.

21. The apparatus according to claim 20 wherein an electrically conductive portion of said spring includes a material selected from the group consisting of stainless steel, beryllium copper, copper, silver, titanium, gold, platinum, palladium, rhenium, tungsten, nickel, cobalt, and alloys thereof.

22. The apparatus according to claim 20 wherein said spring includes an electrically conductive core and an electrically insulating coating.

23. The apparatus according to claim 16 wherein said torsion spring includes a wire having cross-sectional dimensions on a micron scale.

24. The apparatus according to claim 23 wherein said cross-sectional dimensions are between 2 microns and 100 microns.

* * * * *